(12) United States Patent
Shozui et al.

(10) Patent No.: US 9,447,443 B2
(45) Date of Patent: Sep. 20, 2016

(54) METHOD FOR PRODUCING 3-ACETYLAMINO-4-HYDROXYBENZOIC ACID

(71) Applicant: AJINOMOTO CO., INC., Tokyo (JP)

(72) Inventors: Fumi Shozui, Kanagawa (JP); Yoshinori Tajima, Kanagawa (JP); Keiichi Yokoyama, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 14/547,481

(22) Filed: Nov. 19, 2014

(65) Prior Publication Data

US 2015/0079644 A1   Mar. 19, 2015

Related U.S. Application Data

(63) Continuation of application No. PCT/JP2013/056025, filed on Mar. 5, 2013.

(30) Foreign Application Priority Data

May 29, 2012 (JP) .................................. 2012-122388

(51) Int. Cl.
*C12P 13/02* (2006.01)
*C12P 7/22* (2006.01)
*C12P 7/42* (2006.01)
*C12N 9/10* (2006.01)
*C12P 13/00* (2006.01)
*C08G 73/22* (2006.01)

(52) U.S. Cl.
CPC .............. *C12P 13/02* (2013.01); *C08G 73/22* (2013.01); *C12N 9/104* (2013.01); *C12P 13/005* (2013.01); *Y02P 20/52* (2015.11)

(58) Field of Classification Search
None
See application file for complete search history.

(56) References Cited

U.S. PATENT DOCUMENTS

| 8,076,111 | B2 | 12/2011 | Fukui et al. |
| 8,093,346 | B2 | 1/2012 | Suzuki et al. |
| 8,105,802 | B2 | 1/2012 | Umezawa et al. |
| 8,247,201 | B2 | 8/2012 | Tajima et al. |
| 8,367,371 | B2 | 2/2013 | Tajima et al. |
| 8,497,104 | B2 | 7/2013 | Tajima et al. |
| 8,580,537 | B2 | 11/2013 | Suzuki et al. |

| 2010/0112647 | A1 | 5/2010 | Hara et al. |
| 2010/0143970 | A1 | 6/2010 | Yokoyama et al. |
| 2011/0137007 | A1 | 6/2011 | Suzuki et al. |

FOREIGN PATENT DOCUMENTS

| CN | 102089437 A | 6/2011 |
| JP | 2004-283163 | 10/2004 |
| JP | 2008-029325 | 2/2008 |
| WO | WO2010/005099 | 1/2010 |

OTHER PUBLICATIONS

Machine-language translation of JP 2004-283163, 15 pages, obtained from https://www4.j-platpat.inpit.go.jp/eng/tokujitsu/tkbs_en/TKBS_EN_GM101_Top.action on Dec. 9, 2015.*
Josephy et al., Biol. Chem. 383:977-982, 2002.*
Office Action from Chinese Patent App. No. 201380027849.1 (Sep. 28, 2015) with English language translation thereof.
Rude, M. A., et al., "Production of Ansamycin Polyketide Precursors in *Escherichia coli*," J. Antibiot. 2006;59 (8):464-470.
Suzuki, H., et al., "Enzyme Catalysis and Regulation: Novel Benzene Ring Biosynthesis from C3 and C4 Primary Metabolites by Two Enzymes," J. Biol Chem. 2006;281:36944-36951.
Suzuki, H., et al., "Arylamine N-Acetyltransferase Responsible for Acetylation of 2-Aminophenols in Streptomyces griseus," J. Bacteriol. 2007;189(5):2155-2159.
Yamamura, E.-T., et al., "Purification and biochemical properties of an N-hydroxyarylamine O-acetyltransferase from *Escherichia coli*," Biochimica et Biophysica Acta 2000;1475:10-16.
International Search Report for PCT Patent App. No. PCT/JP2013/056025 (Apr. 16, 2013).
Written Opinion for PCT Patent App. No. PCT/JP2013/056025 (Apr. 16, 2013).

* cited by examiner

*Primary Examiner* — David J Steadman
(74) *Attorney, Agent, or Firm* — Shelly Guest Cermak; Cermak Nakajima & McGowan LLP

(57) ABSTRACT

The present invention provides a method for conveniently and efficiently producing a 3-acetylamino-4-hydroxybenzoic acid-type compound that is a stable compound by a process using a microorganism. Specifically the present invention provides a microorganism having an ability to produce 3-amino-4-hydroxybenzoic acid, that is modified so as to increase an activity to form 3-amino-4-hydroxybenzoic acid from dihydroxyacetone phosphate and aspartate semialdehyde, wherein the microorganism is modified so as to increase an N-hydroxyarylamine O-acetyltransferase (NhoA) activity, as well as a method for producing the 3-acetylamino-4-hydroxybenzoic acid-type compound using such a microorganism.

10 Claims, 1 Drawing Sheet

SEQUENCE LISTING

```
<160> NUMBER OF SEQ ID NOS: 23

<210> SEQ ID NO 1
<211> LENGTH: 270
<212> TYPE: PRT
<213> ORGANISM: Streptomyces griseus

<400> SEQUENCE: 1

Met Thr Leu Asp Leu Asp Ala Tyr Phe Ala Arg Ile Gly Trp Thr Gly
1               5                   10                  15

Asn Pro Arg Pro Thr Leu Glu Val Leu Arg Ser Leu His Arg Ala His
            20                  25                  30

Leu Ile Gly Ile Pro Phe Glu Asn Leu Glu Pro Val Leu Gly Ser Ala
        35                  40                  45

Pro Ser Leu Ala Leu Asp Asp Leu Glu Ala Lys Leu Val His Gly Gly
    50                  55                  60

Arg Gly Gly Tyr Cys Tyr Glu His Asn Thr Leu Phe Ser Ala Val Leu
65                  70                  75                  80

Arg Gln Ile Gly Phe Ser Val Thr Pro Leu Thr Ala Arg Val Val Leu
                85                  90                  95

Gly Ala Ala Pro Gly Asp Ile Arg Pro Arg Thr His Met Leu Met Arg
            100                 105                 110

Val Asp Val Ala Gly Glu Pro His Pro Tyr Leu Ala Asp Val Gly Phe
        115                 120                 125

Gly Ala Val Gly Ala Leu Leu Glu Pro Ile Glu Leu Val Glu Asp Ala
    130                 135                 140

Glu Leu Ser Asp Ala Pro Arg Arg His Arg Leu Val His Ala Pro His
145                 150                 155                 160

His Gly Pro Leu Pro Leu Trp Glu Leu Gln Ala Gly Gln Gly Gly Ser
                165                 170                 175

Trp Glu Pro Gln Tyr Asp Phe Thr Leu Asp Pro Tyr Glu Lys Pro Asp
            180                 185                 190

Tyr Glu Val Ile Asn Trp Phe Ile Ala Thr His Pro Arg Ser Pro Phe
        195                 200                 205

Arg Gln Ala Val Tyr Ala Gln Arg Thr Arg Ile Gly Ser His Leu Ala
    210                 215                 220

Leu Ser Gly Leu Asp Leu Val Glu Thr Ala Asp Asp Gly Thr Ile Arg
225                 230                 235                 240

Glu Arg Arg Leu Glu Asp Gly Asp Glu Ala Leu Arg Val Leu Thr Asp
                245                 250                 255

Asp Phe Gly Ile Arg Leu Pro Glu Gly Val Arg Leu Pro Glu
            260                 265                 270

<210> SEQ ID NO 2
```

```
<211> LENGTH: 281
<212> TYPE: PRT
<213> ORGANISM: Escherichia coli

<400> SEQUENCE: 2

Met Thr Pro Ile Leu Asn His Tyr Phe Ala Arg Ile Asn Trp Ser Gly
1               5                   10                  15

Ala Ala Ala Val Asn Ile Asp Thr Leu Arg Ala Leu His Leu Lys His
            20                  25                  30

Asn Cys Thr Ile Pro Phe Glu Asn Leu Asp Val Leu Leu Pro Arg Glu
        35                  40                  45

Ile Gln Leu Asp Asn Gln Ser Pro Glu Glu Lys Leu Val Ile Ala Arg
    50                  55                  60

Arg Gly Gly Tyr Cys Phe Glu Gln Asn Gly Val Phe Glu Arg Val Leu
65                  70                  75                  80

Arg Glu Leu Gly Phe Asn Val Arg Ser Leu Leu Gly Arg Val Val Leu
                85                  90                  95

Ser Asn Pro Pro Ala Leu Pro Pro Arg Thr His Arg Leu Leu Leu Val
            100                 105                 110

Glu Leu Glu Glu Glu Lys Trp Ile Ala Asp Val Gly Phe Gly Gly Gln
        115                 120                 125

Thr Leu Thr Ala Pro Ile Arg Leu Val Ser Asp Leu Val Gln Thr Thr
    130                 135                 140

Pro His Gly Glu Tyr Arg Leu Leu Gln Glu Gly Asp Asp Trp Val Leu
145                 150                 155                 160

Gln Phe Asn His His Gln His Trp Gln Ser Met Tyr Arg Phe Asp Leu
                165                 170                 175

Cys Glu Gln Gln Gln Ser Asp Tyr Val Met Gly Asn Phe Trp Ser Ala
            180                 185                 190

His Trp Pro Gln Ser His Phe Arg His His Leu Leu Met Cys Arg His
        195                 200                 205

Leu Pro Asp Gly Gly Lys Leu Thr Leu Thr Asn Phe His Phe Thr His
    210                 215                 220

Tyr Glu Asn Gly His Ala Val Glu Gln Arg Asn Leu Pro Asp Val Ala
225                 230                 235                 240

Ser Leu Tyr Ala Val Met Gln Glu Gln Phe Gly Leu Gly Val Asp Asp
                245                 250                 255

Ala Lys His Gly Phe Thr Val Asp Glu Leu Ala Leu Val Met Ala Ala
            260                 265                 270

Phe Asp Thr His Pro Glu Ala Gly Lys
        275                 280

<210> SEQ ID NO 3
<211> LENGTH: 846
<212> TYPE: DNA
<213> ORGANISM: Escherichia coli

<400> SEQUENCE: 3
atgacgccca ttctgaatca ctattttgcc cgtattaact ggtcgggagc tgctgcggtc    60
aatattgata cgcttcgtgc attgcacctg aaacacaatt gcaccattcc gtttgaaaac   120
ctcgacgttt tgctgccgag ggaaatacag cttgataatc aatcgccgga agagaaactg   180
gtgatagccc gtcgtggcgg ttactgtttt gagcagaatg gcgtgtttga gcgggtgtta   240
cgcgagctgg ggtttaacgt tcgcagcttg ttagggcgcg tagtgttatc aaatccgcca   300
gcattaccgc cgcgcaccca tcgtttgctg ttggtggaac tggaagagga aaaatggatt   360
```

```
gctgatgtcg gtttcggtgg gcagacgcta accgcgccga ttcgtttagt ttccgatctc    420
gtgcagacca cgccacacgg agagtatcgg ttgttgcagg agggtgatga ttgggtgttg    480
cagtttaatc atcatcagca ttggcagtcg atgtaccgtt ttgatctctg cgagcagcaa    540
caaagcgatt atgtgatggg caatttctgg tcggcgcact ggccgcagtc gcattttcgc    600
catcatttgc tgatgtgccg ccatttgccg gacggcggca agctgacact gaccaatttt    660
cattttaccc attatgaaaa tgggcacgcg gtggagcagc gaaatctacc ggatgtggcg    720
tcattatatg ctgtgatgca agaacagttt ggtctgggcg tggatgatgc gaaacatggc    780
tttaccgtgg atgagttagc gctggtgatg gcggcgtttg atacgcaccc ggaggcggga    840
aaataa                                                               846
```

```
<210> SEQ ID NO 4
<211> LENGTH: 43
<212> TYPE: DNA
<213> ORGANISM: Artificial Sequence
<220> FEATURE:
<223> OTHER INFORMATION: Primer 1 for amplifying a polynucleotide of
      nhoA

<400> SEQUENCE: 4
aaaaagcttg tgagcgaaga aggttttttt aagcgtagtc cgt                       43

<210> SEQ ID NO 5
<211> LENGTH: 39
<212> TYPE: DNA
<213> ORGANISM: Artificial Sequence
<220> FEATURE:
<223> OTHER INFORMATION: Primer 2 for amplifying a polynucleotide of
      nhoA

<400> SEQUENCE: 5
aaagaattct gtatgccgga taaggcgttt acgccgcat                            39

<210> SEQ ID NO 6
<211> LENGTH: 3700
<212> TYPE: DNA
<213> ORGANISM: Artificial Sequence
<220> FEATURE:
<223> OTHER INFORMATION: Nucleotide sequence of pUC19-nhoA

<400> SEQUENCE: 6
gacgaaaggg cctcgtgata cgcctatttt tataggttaa tgtcatgata ataatggttt     60
cttagacgtc aggtggcact tttcggggaa atgtgcgcgg aaccctatt tgtttatttt    120 tctaaataca ttcaaatatg tatccgctca tgagacaata accctgataa atgcttcaat    180
aatattgaaa aaggaagagt atgagtattc aacatttccg tgtcgccctt attcccttt     240 ttgcggcatt ttgccttcct gttttgctc acccagaaac gctggtgaaa gtaaaagatg    300
ctgaagatca gttgggtgca cgagtgggtt acatcgaact ggatctcaac agcggtaaga    360
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
```

```
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc atttttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc ttttttttctg cgcgtaatct   1260 gctgcttgca acaaaaaaa ccaccgctac cagcggtggt ttgtttgccg gatcaagagc   1320
taccaactct tttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agcattgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800
gggggcggag cctatggaaa aacgccagca acgcggcctt tttacggttc ctggccttttt   1860 gctggccttt tgctcacatg ttctttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgccaagctt gtgagcgaag aaggtttttt taagcgtagt ccgtaacgca   2280
ataagtaacg aaattaacgg gattggcgat ttgcgaacgt gatgcatgtc cgcgatcgca   2340
caaaatagcc ggtgcggcgt ctattccagg ttataagttg agaaaaccac taagggaaac   2400
gcctgatgac gcccattctg aatcactatt ttgcccgtat taactggtcg ggagctgctg   2460
cggtcaatat tgatacgctt cgtgcattgc acctgaaaca caattgcacc attccgtttg   2520
aaaacctcga cgttttgctg ccgagggaaa tacagcttga taatcaatcg ccggaagaga   2580
aactggtgat agcccgtcgt ggcggttact gttttgagca gaatggcgtg tttgagcggg   2640
tgttacgcga gctggggttt aacgttcgca gcttgttagg gcgcgtagtg ttatcaaatc   2700
cgccagcatt accgccgcgc acccatcgtt tgctgttggt ggaactggaa gaggaaaaat   2760
ggattgctga tgtcggtttc ggtgggcaga cgctaaccgc gccgattcgt ttagtttccg   2820
atctcgtgca gaccacgcca cacgagagt atcggttgtt gcaggagggt gatgattggg   2880
tgttgcagtt taatcatcat cagcattggc agtcgatgta ccgttttgat ctctgcgagc   2940
agcaacaaag cgattatgtg atgggcaatt tctggtcggc gcactggccg cagtcgcatt   3000
ttcgccatca tttgctgatg tgccgccatt tgccggacgg cggcaagctg acactgacca   3060
attttcattt tacccattat gaaaatgggc acgcggtgga gcagcgaaat ctaccggatg   3120
```

-continued

| | |
|---|---|
| tggcgtcatt atatgctgtg atgcaagaac agtttggtct gggcgtggat gatgcgaaac | 3180 |
| atggctttac cgtggatgag ttagcgctgg tgatggcggc gtttgatacg cacccggagg | 3240 |
| cgggaaaata atttatgtca ggttgccgga tgcggcgtaa acgccttatc cggcatacag | 3300 |
| aattcactgg ccgtcgtttt acaacgtcgt gactgggaaa accctggcgt tacccaactt | 3360 |
| aatcgccttg cagcacatcc ccctttcgcc agctggcgta atagcgaaga ggcccgcacc | 3420 |
| gatcgccctt cccaacagtt gcgcagcctg aatggcgaat ggcgcctgat gcggtatttt | 3480 |
| ctccttacgc atctgtgcgg tatttcacac cgcatatggt gcactctcag tacaatctgc | 3540 |
| tctgatgccg catagttaag ccagccccga cacccgccaa cacccgctga cgcgccctga | 3600 |
| cgggcttgtc tgctcccggc atccgcttac agacaagctg tgaccgtctc cgggagctgc | 3660 |
| atgtgtcaga ggttttcacc gtcatcaccg aaacgcgcga | 3700 |

<210> SEQ ID NO 7
<211> LENGTH: 399
<212> TYPE: DNA
<213> ORGANISM: Artificial Sequence
<220> FEATURE:
<223> OTHER INFORMATION: Nucleotide sequence of Ptac-Ttrp

<400> SEQUENCE: 7

| | |
|---|---|
| ggtaccagat ctccctgttg acaattaatc atcggctcta atgtgtgtgg aatcgtgagc | 60 |
| ggataacaat ttcacacaag gagactcccg ggagccgcca gttccgctgg cggcatttta | 120 |
| actttctttta atgaagccgg aaaaatccta aattcattta atatttatct ttttaccgtt | 180 |
| tcgcttaccc cggtcgaacg tcaacttacg tcatttttcc gcccaacagt aatataatca | 240 |
| aacaaattaa tcccgcaaca taacaccagt aaaatcaata atttttctcta agtcacttat | 300 |
| tcctcaggta attgttaata tatccagaat gttcctcaaa atatattttc cctctatctt | 360 |
| ctcgttgcgc ttaatttgac taattctcat tagggatcc | 399 |

<210> SEQ ID NO 8
<211> LENGTH: 3383
<212> TYPE: DNA
<213> ORGANISM: Artificial Sequence
<220> FEATURE:
<223> OTHER INFORMATION: Nucleotide sequence of pSTV28-Ptac-Ttrp

<400> SEQUENCE: 8

| | |
|---|---|
| cgtatggcaa tgaaagacgg tgagctggtg atatgggata gtgttcaccc ttgttacacc | 60 |
| gttttccatg agcaaactga aacgttttca tcgctctgga gtgaatacca cgacgatttc | 120 |
| cggcagtttc tacacatata ttcgcaagat gtggcgtgtt acggtgaaaa cctggcctat | 180 |
| ttccctaaag ggtttattga gaatatgttt ttcgtctcag ccaatccctg ggtgagtttc | 240 |
| accagttttg atttaaacgt ggccaatatg gacaacttct tcgcccccgt tttcaccatg | 300 |
| ggcaaatatt atacgcaagg cgacaaggtg ctgatgccgc tggcgattca ggttcatcat | 360 |
| gccgtttgtg atggcttcca tgtcggcaga atgcttaatg aattacaaca gtactgcgat | 420 |
| gagtggcagg gcggggcgta atttttttaa ggcagttatt ggtgccctta aacgcctggt | 480 |
| gctacgcctg aataagtgat aataagcgga tgaatgcag aaattcgaaa gcaaattcga | 540 |
| cccggtcgtc ggttcagggc agggtcgtta atagccgct tatgtctatt gctggtttac | 600 |
| cggtttattg actaccggaa gcagtgtgac cgtgtgcttc tcaaatgcct gaggccagtt | 660 |
| tgctcaggct ctccccgtgg aggtaataat tgacgatatg atcatttatt ctgcctccca | 720 |

```
gagcctgata aaaacggtta gcgcttcgtt aatacagatg taggtgttcc acagggtagc    780
cagcagcatc ctgcgatgca gatccggaac ataatggtgc agggcgcttg tttcggcgtg    840
ggtatggtgg caggccccgt ggccggggga ctgttgggcg ctgccggcac ctgtcctacg    900
agttgcatga taaagaagac agtcataagt gcggcgacga tagtcatgcc ccgcgcccac    960
cggaaggagc taccggacag cggtgcggac tgttgtaact cagaataaga aatgaggccg   1020
ctcatggcgt tccaatacgc aaaccgcctc tccccgcgcg ttggccgatt cattaatgca   1080
gctggcacga caggtttccc gactggaaag cgggcagtga gcgcaacgca attaatgtga   1140
gttagctcac tcattaggca ccccaggctt tacactttat gcttccggct cgtatgttgt   1200
gtggaattgt gagcggataa caatttcaca caggaaacag ctatgaccat gattacgaat   1260
tcgagctcgg taccagatct ccctgttgac aattaatcat cggctctata atgtgtggaa   1320
tcgtgagcgg ataacaattt cacacaagga gactcccggg agccgccagt tccgctggcg   1380
gcattttaac tttctttaat gaagccgaaa aaatcctaaa ttcatttaat atttatcttt   1440
ttaccgtttc gcttaccccg tcgaacgtc aacttacgtc attttccgc ccaacagtaa    1500 tataatcaaa caattaatc ccgcaacata acaccagtaa aatcaataat tttctctaag   1560
tcacttattc ctcaggtaat tgttaatata tccagaatgt tcctcaaaat atattttccc   1620
tctatcttct cgttgcgctt aatttgacta attctcatta gggatcctct agagtcgacc   1680
tgcaggcatg caagcttggc actggccgtc gttttacaac gtcgtgactg gaaaacccct   1740
ggcgttaccc aacttaatcg ccttgcagca catccccctt tcgccagctg gcgtaatagc   1800
gaagaggccc gcaccgatcg cccttcccaa cagttgcgca gcctgaatgg cgaatgagct   1860
tatcgatgat aagctgtcaa acatgagaat acaacttat atcgtatggg gctgacttca   1920
ggtgctacat ttgaagagat aaattgcact gaaatctaga aatatttat ctgattaata   1980 agatgatctt cttgagatcg ttttggtctg cgcgtaatct cttgctctga aaacgaaaaa   2040
accgccttgc agggcggttt ttcgaaggtt ctctgagcta ccaactcttt gaaccgaggt   2100
aactggcttg gaggagcgca gtcaccaaaa cttgtccttt cagtttagcc ttaaccggcg   2160
catgacttca agactaactc ctctaaatca attaccagtg gctgctgcca gtggtgcttt   2220
tgcatgtctt tccgggttgg actcaagacg atagttaccg gataaggcgc agcggtcgga   2280
ctgaacgggg ggttcgtgca tacagtccag cttgagcga actgcctacc cggaactgag   2340
tgtcaggcgt ggaatgagac aaacgcggcc ataacagcgg aatgacaccg gtaaaccgaa   2400
aggcaggaac aggagagcgc acgagggagc cgccagggga aacgcctggt atctttatag   2460
tcctgtcggg tttcgccacc actgatttga gcgtcagatt tcgtgatgct tgtcaggggg   2520
gcggagccta tggaaaaacg gctttgccgc ggccctctca cttccctgtt aagtatcttc   2580
ctggcatctt ccaggaaatc tccgccccgt tcgtaagcca tttccgctcg ccgcagtcga   2640
acgaccgagc gtagcgagtc agtgagcgag gaagcggaat atatcctgta tcacatattc   2700
tgctgacgca ccggtgcagc cttttttctc ctgccacatg aagcacttca ctgacaccct   2760
catcagtgcc aacatagtaa gccagtatac actccgctag cgctgatgtc cggcggtgct   2820
tttgccgtta cgcaccaccc cgtcagtagc tgaacaggag ggacagctga tagaaacaga   2880
agccactgga gcacctcaaa aacaccatca tacactaaat cagtaagttg gcagcatcac   2940
ccgacgcact ttgcgccgaa taaataccctg tgacggaaga tcacttcgca gaataaataa   3000
atcctggtgt ccctgttgat accgggaagc cctgggccaa cttttggcga aaatgagacg   3060
ttgatcggca cgtaagaggt tccaactttc accataatga aataagatca ctaccgggcg   3120
```

-continued

```
tattttttga gttatcgaga ttttcaggag ctaaggaagc taaaatggag aaaaaaatca    3180
ctggatatac caccgttgat atatcccaat ggcatcgtaa agaacatttt gaggcatttc    3240
agtcagttgc tcaatgtacc tataaccaga ccgttcagct ggatattacg gccttttaa    3300 agaccgtaaa gaaaataag cacaagtttt atccggcctt tattcacatt cttgcccgcc     3360
tgatgaatgc tcatccggaa ttt                                             3383
```

<210> SEQ ID NO 9
<211> LENGTH: 274
<212> TYPE: PRT
<213> ORGANISM: Streptomyces griseus

<400> SEQUENCE: 9

```
Met Ala Pro Asn Ala Pro Phe Ala Arg Ser Leu Arg Leu Gln Arg Leu
 1               5                  10                  15

His His His Asp Pro Asp Arg Leu Phe Ile Val Pro Leu Asp His Ser
            20                  25                  30

Ile Thr Asp Gly Pro Leu Ser Arg Ala His Arg Leu Asp Pro Leu Val
        35                  40                  45

Gly Glu Leu Ala Ser His His Val Asp Gly Ile Val Leu His Lys Gly
    50                  55                  60

Ser Leu Arg His Val Asp Pro Glu Trp Phe Thr Arg Thr Ser Leu Ile
65                  70                  75                  80

Val His Leu Ser Ala Ser Thr Val His Ala Pro Asp Pro Asn Ala Lys
                85                  90                  95

Tyr Leu Val Ser Ser Val Glu Ser Leu Arg Met Gly Ala Asp Ala
            100                 105                 110

Val Ser Val His Val Asn Leu Gly Ser Glu Gly Glu Arg His Gln Ile
        115                 120                 125

Ala Asp Met Ala Ala Val Ala Glu Ala Cys Asp Arg Trp Asn Val Pro
    130                 135                 140

Leu Leu Ala Met Met Tyr Pro Arg Gly Pro Lys Ile Asp Asp Pro Arg
145                 150                 155                 160

Asp Pro Ala Leu Val Ala His Ala Val Gln Val Ala Val Asp Leu Gly
                165                 170                 175

Ala Asp Leu Val Lys Thr Leu Tyr Val Gly Ser Val Ala Ala Met Ala
            180                 185                 190

Glu Ile Thr Ala Ala Ser Pro Val Pro Val Val Val Gly Gly Pro
        195                 200                 205

Arg Asp Ser Asp Glu Ser Arg Ile Leu Ala Tyr Val Asp Ala Leu
    210                 215                 220

Arg Gly Gly Ala Ala Gly Val Ala Met Gly Arg Asn Val Phe Gln Ala
225                 230                 235                 240

Pro Asp Pro Gly Ala Met Ala Asp Lys Leu Ser Asp Leu Ile His Asn
                245                 250                 255

Ser Gly Thr Arg Gly Ala Ala Arg Ala Pro Ala Gly Ala Ala Gly
            260                 265                 270

Ala Ala
```

<210> SEQ ID NO 10
<211> LENGTH: 825
<212> TYPE: DNA
<213> ORGANISM: Streptomyces griseus

<400> SEQUENCE: 10

-continued

```
atggccccga acgcgccctt cgccaggagt ctgcgactcc agcggctcca tcaccacgac    60
cccgaccggc tgttcatcgt gccgctcgac cactcgatca ccgacggccc gctgagccgt   120
gcccaccgcc tcgacccgct cgtcggcgaa ctggcctccc accacgtcga cgggatcgtc   180
ctgcacaagg gctcgctgcg ccacgtggac cggagtggt tcacgcggac ctcgctgatc    240
gtgcacctca gcgccagcac cgtgcacgcg cccgacccga cgccaagta cctggtgtcg    300
agcgtcgagg agagcctgcg catgggcgcg gacgcggtga cgtccacgt caatctcggc    360
tccgaggggg aacgccacca gatcgcggac atggcggcgg tcgcggaggc ctgcgaccgc   420
tggaacgtac cgctgctggc gatgatgtat ccgcgcggcc ccaagatcga cgacccgcgc   480
gatccggcgc tcgtcgccca tgccgtccag gtggccgtgg acctcggcgc cgacctggtc   540
aagacgctgt acgtcggatc ggtcgcggcg atggccgaga tcaccgcggc ctcgcccgtt   600
ccggtcgtcg tggtcggcgg accgcgcgac agtgacgaga gccggatcct cgcctacgtc   660
gacgacgcgc tgcgcggcgg cgcggccggt gtcgccatgg ccgcaacgt cttccaggcc    720
cctgatcccg gcgcgatggc ggacaagctc tccgacctca tccacaacag cggcaccagg   780
ggcgcggccc gggctccggc cggcgccgcc gccggagccg cctga                   825
```

<210> SEQ ID NO 11
<211> LENGTH: 396
<212> TYPE: PRT
<213> ORGANISM: Streptomyces griseus

<400> SEQUENCE: 11

```
Met Ser Ser Ser Pro Ser Pro Ser Ser Ser Ser Ser Ser
1               5                   10                  15

Ala Ser Ser Ala Ser Ser Ser Pro Ser Ser Ser Lys Leu Thr
            20                  25                  30

Trp Leu Asp Ile Arg Ser Val Gly Glu Ala Arg Ala Ile Val Gln
        35                  40                  45

Glu Ala Leu His His Arg Val Glu Ala Leu Val Ala Asp Asp Pro Ala
    50                  55                  60

His Leu Ala Asp Leu Pro Pro Thr Val Ala Lys Val Leu Leu Val
65                  70                  75                  80

Gly Lys Gln Ile Pro Glu Glu Phe Gly Glu Ala Thr Val Val Val
                85                  90                  95

Asp Pro Ser Lys His Gly Val Thr Pro Ala Glu Leu Ala Leu Lys His
            100                 105                 110

Pro Glu Ile Glu Phe Gly Arg Phe Val Glu Ile Ile Asp Ala Pro Thr
        115                 120                 125

Leu Glu Asp Ala Cys Glu Ser Ser Arg Thr Glu Lys Trp Ser Val Leu
    130                 135                 140

Leu Phe Arg Asp Pro Thr Lys Ile Pro Leu Glu Ile Val Ile Ala Ala
145                 150                 155                 160

Ala Ala Arg Ala Ser Gly Ser Met Val Thr Ile Ala Gln Asp Leu Glu
                165                 170                 175

Glu Ala Glu Ile Leu Phe Gly Val Leu Glu His Gly Ser Asp Gly Val
            180                 185                 190

Met Met Ala Pro Lys Thr Val Gly Asp Ala Ala Glu Leu Lys Arg Ile
        195                 200                 205

Ala Glu Ala Gly Ile Pro Asn Leu Asn Leu Thr Glu Leu Arg Val Val
    210                 215                 220
```

```
Glu Thr Ser His Ile Gly Met Gly Glu Arg Ala Cys Val Asp Thr Thr
225                 230                 235                 240

Thr His Phe Gly Glu Asp Glu Gly Ile Leu Val Gly Ser His Ser Lys
            245                 250                 255

Gly Met Ile Leu Cys Val Ser Glu Thr His Pro Leu Pro Tyr Met Pro
        260                 265                 270

Thr Arg Pro Phe Arg Val Asn Ala Gly Ala Ile His Ser Tyr Thr Leu
    275                 280                 285

Gly Arg Asp Glu Arg Thr Asn Tyr Leu Ser Glu Leu Lys Thr Gly Ser
290                 295                 300

Lys Leu Thr Ala Val Asp Ile Lys Gly Asn Thr Arg Leu Val Thr Val
305                 310                 315                 320

Gly Arg Val Lys Ile Glu Thr Arg Pro Leu Ile Ser Ile Asp Ala Glu
            325                 330                 335

Ala Pro Asp Gly Arg Arg Val Asn Leu Ile Leu Gln Asp Asp Trp His
        340                 345                 350

Val Arg Val Leu Gly Pro Gly Gly Thr Val Leu Asn Ser Thr Glu Leu
    355                 360                 365

Lys Pro Gly Asp Thr Val Leu Gly Tyr Leu Pro Val Glu Asp Arg His
370                 375                 380

Val Gly Tyr Pro Ile Asn Glu Phe Cys Leu Glu Lys
385                 390                 395

<210> SEQ ID NO 12
<211> LENGTH: 1191
<212> TYPE: DNA
<213> ORGANISM: Streptomyces griseus

<400> SEQUENCE: 12
atgtcttcgt ctccgtctcc gtctccgtcc tcgtcgtcct cgtcatctgc gtcctcgtcg     60
gcttcgtcgt cgccttcgtc gtcgtcgaag ctgacctggc tcgacatccg ttccgtgggc    120
gaggcccgtg ccgccatcgt ccaggaggcc ctgcaccacc gggtggaagc gctggtcgcc    180
gacgaccccg cccacctcgc ggacctgccg cccaccgtgg ccaaggtcct gctggtggtg    240
gggaagcaga tcccggagga gttcggcgag gcgacggtcg tcgtcgtcga cccgtcgaag    300
cacggtgtga cccccgccga actggcgctc aagcacccgg agatcgagtt cgggcggttc    360
gtggagatca tcgacgcgcc gacgctggag acgcctgcg agtcctcgcg gaccgagaag    420
tggtccgtcc tgctgttccg cgacccgacc aagatcccgc tggagatcgt gatcgccgcc    480
gccgcgcgcg cctccggttc gatggtgacc atcgcgcagg acctggagga ggcggagatc    540
ctcttcggcg tgctggagca cggctcggac ggcgtgatga tggccccgaa cggtcggt     600 gacgccgccg agctgaagcg gatcgccgag gccggcatcc ccaacctcaa cctcaccgag    660
ctgcgcgtcg tggagaccag ccacatcggc atgggcgagc gggcctgcgt ggacaccacc    720
acgcatttcg gcgaggacga gggcatcctg gtcggctcgc actccaaggg catgatcctc    780
tgcgtcagcg agacccaccc gctgccgtac atgccgaccc ggccgttccg cgtcaacgcc    840
ggcgccatcc actcgtacac gctgggcagg gacgagcgca cgaactacct gagcgaactg    900
aagacgggca gcaagctcac cgccgtcgac atcaagggca acaccggct ggtgaccgtg    960 ggccgcgtga agatcgagac ccgcccgctg atctccatcg acgccgaggc cccggacggc   1020
cggcgcgtca acctgatcct ccaggacgac tggcacgtcc gggtcctcgg ccccggtggc   1080
acggtcctca acagcaccga gctgaagccc ggcgacacgg tcctcggcta cctgcccgtc   1140
```
gaggaccgtc acgtcggcta cccgatcaac gagttctgcc tggagaagta g    1191

<210> SEQ ID NO 13
<211> LENGTH: 2480
<212> TYPE: DNA
<213> ORGANISM: Artificial Sequence
<220> FEATURE:
<223> OTHER INFORMATION: Nucleotide sequence of EcGriIH

<400> SEQUENCE: 13
gaattcgagc tcggtaccag atctccctgt tgacaattaa tcatcggctc tataatgtgt    60
ggaatcgtga gcggataaca atttcacaca aggagactcc catggccccg aatgccccgt   120
ttgctcgtag cctgcgcctg caacgcctgc accaccatga cccggatcgc ctgttcatcg   180
tcccgctgga tcatagcatt accgacggtc cgctgtctcg tgcacaccgc ctggatccgc   240
tggttggcga actggcaagc catcacgtcg acggcattgt gctgcataaa ggttctctgc   300
gtcacgtgga tccggaatgg tttacccgca cgtcactgat cgtgcatctg agtgcgtcca   360
cggttcacgc cccggatccg aacgcaaaat atctggttag ctctgtcgaa gaatccctgc   420
gtatgggcgc ggatgccgtt agtgtccatg tgaatctggg ctccgaaggt gaacgtcacc   480
agattgcaga tatggcagca gtcgcagaag cgtgcgaccg ttggaacgtt ccgctgctgg   540
cgatgatgta ccgcgtggt ccgaaaatcg atgacccgcg tgatccggcc ctggtggcgc   600
atgccgttca gtcgctgtg gatctgggcg cggacctggt taaaaccctg tacgtgggtt   660
cagttgcagc tatggcagaa attacggcag catcgccggt gccggtggtt gtcgtgggcg   720
gtccgcgtga ttcagacgaa tcgcgcatcc tggcctacgt tgatgacgca ctgcgtggcg   780
gtgcagctgg tgttgctatg ggtcgcaatg tcttccaggc accggatccg ggtgcaatgg   840
ctgataaact gagcgacctg atccacaatt caggtacccg tggtgctgcc cgtgctccgg   900
ctggtgccgc cgctggtgct gcgtgataac ccaggagact cgaatgtcaa gttccccgtc   960
accgtcaccg tcatcttctt cctcgtcaag tgcaagttcc agtgcctctt caagtccgtc  1020
aagttcaagt aaactgacct ggctggatat cgtagcgtg ggtgaagcac gtgcagcaat  1080
cgttcaggaa gccctgcatc accgtgtcga agcactggtg gctgatgacc cggcacacct  1140
ggcagatctg ccgccgaccg tgcaaaagt tctgctggtt gtgggtaaac aaattccgga  1200
agaatttggc gaagcgacgg tcgtggttgt cgatccgtca aaacatggtg tgaccccggc  1260
agaactggct ctgaaacacc cggaaatcga atttggccgc ttcgttgaaa ttatcgatgc  1320
gccgacgctg gaagacgcct gcgaaagctc tcgcaccgaa aaatggtccg tgctgctgtt  1380
tcgtgatccg acgaaaattc cgctggaaat tgttatcgca gctgcggccc gtgccagtgg  1440
ttccatggtc accattgcac aggacctgga agaagctgaa atcctgttcg gcgttctgga  1500
acacggcagc gatggtgtta tgatggcacc gaaaaccgtc ggtgacgcag ctgaactgaa  1560
acgcattgcg gaagccggca tcccgaacct gaatctgacg gaactgcgcg tggttgaaac  1620
ctctcatatt ggcatgggtg aacgtgcgtg cgtggatacc acgacccatt ttggcgaaga  1680
cgaaggtatt ctggtcggct cacactcgaa gggtatgatc ctgtgtgtga gtgaaacgca  1740
tccgctgccg tatatgccga cccgtccgtt ccgtgtgaac gcaggtgcta tccactccta  1800
tacgctgggc cgtgatgaac gcaccaatta cctgagcgaa ctgaaaacgg ctctaaaact  1860
gaccgccgtc gacattaagg gtaacacgcg tctggtcacc gtgggccgcg ttaaaatcga  1920
aacccgtccg ctgatttcaa tcgatgcaga agcaccggac ggtcgtcgcg tgaacctgat  1980
tctgcaagat gactggcatg ttcgtgtcct gggtccgggc ggtacggtgc tgaacagcac  2040

```
cgaactgaaa ccgggtgata ccgttctggg ctacctgccg gtcgaagatc gccatgtggg    2100
ctatccgatc aacgaatttt gtctggaaaa ataataaccc gggagccgcc agttccgctg    2160
gcggcatttt aactttcttt aatgaagccg gaaaaatcct aaattcattt aatatttatc    2220
tttttaccgt ttcgcttacc ccggtcgaac gtcaacttac gtcattttc cgcccaacag     2280 taatataatc aaacaaatta atcccgcaac ataaccag taaaatcaat aattttctct      2340
aagtcactta ttcctcaggt aattgttaat atatccagaa tgttcctcaa aatatatttt    2400
ccctctatct tctcgttgcg cttaatttga ctaattctca ttagggatcc tctagagtcg    2460
acctgcaggc atgcaagctt                                                2480

<210> SEQ ID NO 14
<211> LENGTH: 5109
<212> TYPE: DNA
<213> ORGANISM: Artificial Sequence
<220> FEATURE:
<223> OTHER INFORMATION: Nucleotide sequence of pUC57-EcGri

<400> SEQUENCE: 14
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgagctcggt accagatctc    420
cctgttgaca attaatcatc ggctctataa tgtgtggaat cgtgagcgga taacaatttc    480
acacaaggag actcccatgg ccccgaatgc cccgtttgct cgtagcctgc gcctgcaacg    540
cctgcaccac catgacccgg atcgcctgtt catcgtcccg ctggatcata gcattaccga    600
cggtccgctg tctcgtgcac accgcctgga tccgctggtt ggcgaactgg caagccatca    660
cgtcgacggc attgtgctgc ataaaggttc tctgcgtcac gtggatccgg aatggtttac    720
ccgcacgtca ctgatcgtgc atctgagtgc gtccacggtt cacgccccgg atccgaacgc    780
aaaatatctg gttagctctg tcgaagaatc cctgcgtatg ggcgcggatg ccgttagtgt    840
ccatgtgaat ctgggctccg aaggtgaacg tcaccagatt gcagatatgg cagcagtcgc    900
agaagcgtgc gaccgttgga acgttccgct gctggcgatg atgtatcgc gtggtccgaa     960 aatcgatgac ccgcgtgatc cggccctggt ggcgcatgcc gttcaagtcg ctgtggatct    1020
gggcgcggac ctggttaaaa ccctgtacgt gggttcagtt gcagctatgg cagaaattac    1080
ggcagcatcg ccggtgccgg tggttgtcgt gggcggtccg cgtgattcag acgaatcgcg    1140
catcctggcc tacgttgatg acgcactgcg tggcggtgca gctggtgttg ctatgggtcg    1200
caatgtcttc caggcaccgg atccgggtgc aatggctgat aaactgagcg acctgatcca    1260
caattcaggt accgtggtg ctgccgtgc tccggctggt gccgccgctg gtgctgcgtg      1320
ataacccagg agactcgaat gtcaagttcc ccgtcaccgt caccgtcatc ttcttcctcg    1380
tcaagtgcaa gttccagtgc ctcttcaagt ccgtcaagtt caagtaaact gacctggctg    1440
gatattcgta gcgtgggtga agcacgtgca gcaatcgttc aggaagccct gcatcaccgt    1500
gtcgaagcac tggtggctga tgacccggca cacctggcag atctgccgcc gaccgtggca    1560
```

```
aaagttctgc tggttgtggg taaacaaatt ccggaagaat ttggcgaagc gacggtcgtg    1620
gttgtcgatc cgtcaaaaca tggtgtgacc ccggcagaac tggctctgaa acacccggaa    1680
atcgaatttg gccgcttcgt tgaaattatc gatgcgccga cgctggaaga cgcctgcgaa    1740
agctctcgca ccgaaaaatg gtccgtgctg ctgtttcgtg atccgacgaa aattccgctg    1800
gaaattgtta tcgcagctgc ggcccgtgcc agtggttcca tggtcaccat tgcacaggac    1860
ctggaagaag ctgaaatcct gttcggcgtt ctggaacacg gcagcgatgg tgttatgatg    1920
gcaccgaaaa ccgtcggtga cgcagctgaa ctgaaacgca ttgcggaagc cggcatcccg    1980
aacctgaatc tgacggaact cgcgtggtt gaaacctctc atattggcat gggtgaacgt    2040
gcgtgcgtgg ataccacgac ccattttggc gaagacgaag gtattctggt cggctcacac    2100
tcgaagggta tgatcctgtg tgtgagtgaa acgcatccgc tgccgtatat gccgacccgt    2160
ccgttccgtg tgaacgcagg tgctatccac tcctatacgc tgggccgtga tgaacgcacc    2220
aattacctga gcgaactgaa acgggctct aaactgaccg ccgtcgacat taagggtaac    2280
acgcgtctgg tcaccgtggg ccgcgttaaa atcgaaaccc gtccgctgat ttcaatcgat    2340
gcagaagcac cggacggtcg tcgcgtgaac ctgattctgc aagatgactg gcatgttcgt    2400
gtcctgggtc cgggcggtac ggtgctgaac agcaccgaac tgaaaccggg tgataccgtt    2460
ctgggctacc tgccggtcga agatcgccat gtgggctatc cgatcaacga attttgtctg    2520
gaaaaataat aacccgggag ccgccagttc cgctggcggc attttaactt tctttaatga    2580
agccggaaaa atcctaaatt catttaatat ttatcttttt accgtttcgc ttaccccggt    2640
cgaacgtcaa cttacgtcat ttttccgccc aacagtaata taatcaaaca aattaatccc    2700
gcaacataac accagtaaaa tcaataattt tctctaagtc acttattcct caggtaattg    2760
ttaatatatc cagaatgttc ctcaaaatat attttccctc tatcttctcg ttgcgcttaa    2820
tttgactaat tctcattagg gatcctctag agtcgacctg caggcatgca agcttggcgt    2880
aatcatggtc atagctgttt cctgtgtgaa attgttatcc gctcacaatt ccacacaaca    2940
tacgagccgg aagcataaag tgtaaagcct ggggtgccta atgagtgagc taactcacat    3000
taattgcgtt gcgctcactg cccgctttcc agtcgggaaa cctgtcgtgc cagctgcatt    3060
aatgaatcgg ccaacgcgcg gggagaggcg gtttgcgtat tgggcgctct tccgcttcct    3120
cgctcactga ctcgctgcgc tcggtcgttc ggctgcggcg agcggtatca gctcactcaa    3180
aggcggtaat acggttatcc acagaatcag gggataacgc aggaaagaac atgtgagcaa    3240
aaggccagca aaaggccagg aaccgtaaaa aggccgcgtt gctggcgttt ttccataggc    3300
tccgcccccc tgacgagcat cacaaaaatc gacgctcaag tcagaggtgg cgaaacccga    3360
caggactata aagataccag gcgtttcccc ctggaagctc cctcgtgcgc tctcctgttc    3420
cgaccctgcc gcttaccgga tacctgtccg cctttctccc ttcgggaagc gtggcgcttt    3480
ctcatagctc acgctgtagg tatctcagtt cggtgtaggt cgttcgctcc aagctgggct    3540
gtgtgcacga accccccgtt cagcccgacc gctgcgcctt atccggtaac tatcgtcttg    3600
agtccaaccc ggtaagacac gacttatcgc cactggcagc agccactggt aacaggatta    3660
gcagagcgag gtatgtaggc ggtgctacag agttcttgaa gtggtggcct aactacggct    3720
acactagaag aacagtattt ggtatctgcg ctctgctgaa gccagttacc ttcggaaaaa    3780
gagttggtag ctcttgatcc ggcaaacaaa ccaccgctgg tagcggtggt ttttttgttt    3840
gcaagcagca gattacgcgc agaaaaaaag gatctcaaga agatcctttg atcttttcta    3900
cggggtctga cgctcagtgg aacgaaaact cacgttaagg gattttggtc atgagattat    3960
```

```
caaaaaggat cttcacctag atccttttaa attaaaaatg aagttttaaa tcaatctaaa    4020
gtatatatga gtaaacttgg tctgacagtt accaatgctt aatcagtgag gcacctatct    4080
cagcgatctg tctatttcgt tcatccatag ttgcctgact ccccgtcgtg tagataacta    4140
cgatacggga gggcttacca tctggcccca gtgctgcaat gataccgcga gacccacgct    4200
caccggctcc agatttatca gcaataaacc agccagccgg aagggccgag cgcagaagtg    4260
gtcctgcaac tttatccgcc tccatccagt ctattaattg ttgccgggaa gctagagtaa    4320
gtagttcgcc agttaatagt ttgcgcaacg ttgttgccat tgctacaggc atcgtggtgt    4380
cacgctcgtc gtttggtatg gcttcattca gctccggttc ccaacgatca aggcgagtta    4440
catgatcccc catgttgtgc aaaaaagcgg ttagctcctt cggtcctccg atcgttgtca    4500
gaagtaagtt ggccgcagtg ttatcactca tggttatggc agcactgcat aattctctta    4560
ctgtcatgcc atccgtaaga tgcttttctg tgactggtga gtactcaacc aagtcattct    4620
gagaatagtg tatgcggcga ccgagttgct cttgcccggc gtcaatacgg gataataccg    4680
cgccacatag cagaacttta aaagtgctca tcattggaaa acgttcttcg ggcgaaaac     4740 tctcaaggat cttaccgctg ttgagatcca gttcgatgta acccactcgt gcacccaact    4800
gatcttcagc atcttttact ttcaccagcg tttctgggtg agcaaaaaca ggaaggcaaa    4860
atgccgcaaa aaagggaata agggcgacac ggaaatgttg aatactcata ctcttccttt    4920
ttcaatatta ttgaagcatt tatcagggtt attgtctcat gagcggatac atatttgaat    4980
gtatttagaa aaataaacaa ataggggttc cgcgcacatt tccccgaaaa gtgccacctg    5040
acgtctaaga aaccattatt atcatgacat taacctataa aaataggcgt atcacgaggc    5100
cctttcgtc                                                           5109

<210> SEQ ID NO 15
<211> LENGTH: 39
<212> TYPE: DNA
<213> ORGANISM: Artificial Sequence
<220> FEATURE:
<223> OTHER INFORMATION: Primer 1 for amplifying a polynucleotide of
      EcGri

<400> SEQUENCE: 15
cacaaggaga ctcccatggc cccgaatgcc ccgtttgct                            39

<210> SEQ ID NO 16
<211> LENGTH: 45
<212> TYPE: DNA
<213> ORGANISM: Artificial Sequence
<220> FEATURE:
<223> OTHER INFORMATION: Primer 2 for amplifying a polynucleotide of
      EcGri

<400> SEQUENCE: 16
gaactggcgg ctcccgggtt attattttc cagacaaaat tcgtt                      45

<210> SEQ ID NO 17
<211> LENGTH: 5411
<212> TYPE: DNA
<213> ORGANISM: Artificial Sequence
<220> FEATURE:
<223> OTHER INFORMATION: Nucleotide sequence of pSTV28-EcGri

<400> SEQUENCE: 17
cgtatggcaa tgaaagacgg tgagctggtg atatgggata gtgttcaccc ttgttacacc    60
```

```
gttttccatg agcaaactga aacgttttca tcgctctgga gtgaatacca cgacgatttc    120
cggcagtttc tacacatata ttcgcaagat gtggcgtgtt acggtgaaaa cctggcctat    180
ttccctaaag ggtttattga gaatatgttt ttcgtctcag ccaatccctg ggtgagtttc    240
accagttttg atttaaacgt ggccaatatg gacaacttct tcgcccccgt tttcaccatg    300
ggcaaatatt atacgcaagg cgacaaggtg ctgatgccgc tggcgattca ggttcatcat    360 gccgttgtg atggcttcca tgtcggcaga atgcttaatg aattacaaca gtactgcgat    420
gagtggcagg gcggggcgta atttttttaa ggcagttatt ggtgcccttta acgcctggt    480 gctacgcctg aataagtgat aataagcgga tgaatggcag aaattcgaaa gcaaattcga    540
cccggtcgtc ggttcagggc agggtcgtta atagccgct tatgtctatt gctggtttac    600
cggtttattg actaccggaa gcagtgtgac cgtgtgcttc tcaaatgcct gaggccagtt    660
tgctcaggct ctccccgtgg aggtaataat tgacgatatg atcatttatt ctgcctccca    720
gagcctgata aaaacggtta gcgcttcgtt aatacagatg taggtgttcc acagggtagc    780
cagcagcatc ctgcgatgca gatccggaac ataatggtgc agggcgcttg tttcggcgtg    840
ggtatggtgg caggccccgt ggccgggga ctgttgggcg ctgccggcac ctgtcctacg    900
agttgcatga taaagaagac agtcataagt gcggcgacga tagtcatgcc ccgcgcccac    960
cggaaggagc taccggacag cggtgcggac tgttgtaact cagaataaga aatgaggccg   1020
ctcatggcgt tccaatacgc aaaccgcctc tccccgcgcg ttggccgatt cattaatgca   1080
gctggcacga caggtttccc gactggaaag cgggcagtga gcgcaacgca attaatgtga   1140
gttagctcac tcattaggca ccccaggctt tacactttat gcttccggct cgtatgttgt   1200
gtggaattgt gagcggataa caatttcaca caggaaacag ctatgaccat gattacgaat   1260
tcgagctcgg taccagatct ccctgttgac aattaatcat cggctctata atgtgtggaa   1320
tcgtgagcgg ataacaattt cacacaagga gactcccatg ccccgaatg ccccgtttgc   1380 tcgtagcctg cgcctgcaac gcctgcacca ccatgacccg gatcgcctgt tcatcgtccc   1440
gctggatcat agcattaccg acggtccgct gtctcgtgca caccgcctgg atccgctggt   1500
tggcgaactg gcaagccatc acgtcgacgg cattgtgctg cataaaggtt ctctgcgtca   1560
cgtggatccg gaatggttta cccgcacgtc actgatcgtg catctgagtg cgtccacggt   1620
tcacgccccg gatccgaacg caaaatatct ggttagctct gtcgaagaat ccctgcgtat   1680
gggcgcggat gccgttagtg tccatgtgaa tctgggctcc gaaggtgaac gtcaccagat   1740
tgcagatatg gcagcagtcg cagaagcgtg cgaccgttgg aacgttccgc tgctggcgat   1800
gatgtatccg cgtggtccga aaatcgatga cccgcgtgat ccggccctgg tggcgcatgc   1860
cgttcaagtc gctgtggatc tgggcgcgga cctggttaaa accctgtacg tgggttcagt   1920
tgcagctatg gcagaaatta cggcagcatc gccggtgccg gtggttgtcg tgggcggtcc   1980
gcgtgattca gacgaatcgc gcatcctggc ctacgttgat gacgcactgc gtggcggtgc   2040
agctggtgtt gctatgggtc gcaatgtctt ccaggcaccg gatccgggtg caatggctga   2100
taaactgagc gacctgatcc acaattcagg taccgtggt gctgcccgtg ctccggctgg   2160
tgccgccgct ggtgctgcgt gataacccat gtcaagttcc ccgtcaccgt caccgtcatc   2220
ttcttcctcg tcaagtgcaa gttccagtgc ctcttcaagt ccgtcaagtt caagtaaact   2280
gacctggctg gatattcgta gcgtgggtga agcacgtgca gcaatcgttc aggaagccct   2340
gcatcaccgt gtcgaagcac tggtggctga tgacccggca cacctggcag atctgccgcc   2400
gaccgtggca aaagttctgc tggttgtggg taaacaaatt ccggaagaat ttggcgaagc   2460
```

```
gacggtcgtg gttgtcgatc cgtcaaaaca tggtgtgacc ccggcagaac tggctctgaa    2520
acacccggaa atcgaatttg gccgcttcgt tgaaattatc gatgcgccga cgctggaaga    2580
cgcctgcgaa agctctcgca ccgaaaaatg gtccgtgctg ctgtttcgtg atccgacgaa    2640
aattccgctg gaaattgtta tcgcagctgc ggcccgtgcc agtggttcca tggtcaccat    2700
tgcacaggac ctggaagaag ctgaaatcct gttcggcgtt ctggaacacg gcagcgatgg    2760
tgttatgatg gcaccgaaaa ccgtcggtga cgcagctgaa ctgaaacgca ttgcggaagc    2820
cggcatcccg aacctgaatc tgacggaact gcgcgtggtt gaaacctctc atattggcat    2880
gggtgaacgt gcgtgcgtgg ataccacgac ccatttggc gaagacgaag gtattctggt    2940
cggctcacac tcgaagggta tgatcctgtg tgtgagtgaa acgcatccgc tgccgtatat    3000
gccgacccgt ccgttccgtg tgaacgcagg tgctatccac tcctatacgc tgggccgtga    3060
tgaacgcacc aattacctga gcgaactgaa acgggctct aaactgaccg ccgtcgacat    3120
taagggtaac acgcgtctgg tcaccgtggg ccgcgttaaa atcgaaaccc gtccgctgat    3180
ttcaatcgat gcagaagcac cggacggtcg tcgcgtgaac ctgattctgc aagatgactg    3240
gcatgttcgt gtcctgggtc cgggcggtac ggtgctgaac agcaccgaac tgaaaccggg    3300
tgataccgtt ctgggctacc tgccggtcga agatcgccat gtgggctatc cgatcaacga    3360
attttgtctg gaaaaataat aacccgggag ccgccagttc cgctggcggc atttaacttt    3420
tctttaatga agccggaaaa atcctaaatt catttaatat ttatcttttt accgtttcgc    3480 ttacccggt cgaacgtcaa cttacgtcat ttttccgccc aacagtaata taatcaaaca    3540
aattaatccc gcaacataac accagtaaaa tcataatttt tctctaagtc acttattcct    3600
caggtaattg ttaatatatc cagaatgttc ctcaaaatat attttccctc tatcttctcg    3660
ttgcgcttaa tttgactaat tctcattagg gatcctctag agtcgacctg caggcatgca    3720
agcttggcac tggccgtcgt tttacaacgt cgtgactggg aaaaccctgg cgttacccaa    3780
cttaatcgcc ttgcagcaca tccccctttc gccagctggc gtaatagcga agaggcccgc    3840
accgatcgcc cttcccaaca gttgcgcagc ctgaatggcg aatgagctta tcgatgataa    3900
gctgtcaaac atgagaatta caacttatat cgtatgggc tgacttcagg tgctacattt    3960
gaagagataa attgcactga aatctagaaa tatttatct gattaataag atgatcttct    4020
tgagatcgtt ttggtctgcg cgtaatctct tgctctgaaa acgaaaaaac cgccttgcag    4080
ggcggttttt cgaaggttct ctgagctacc aactctttga accgaggtaa ctggcttgga    4140
ggagcgcagt caccaaaact tgtcctttca gtttagcctt aaccggcgca tgacttcaag    4200
actaactcct ctaaatcaat taccagtggc tgctgccagt ggtgcttttg catgtctttc    4260
cgggttggac tcaagacgat agttaccgga taaggcgcag cggtcggact gaacggggggg    4320 ttcgtgcata cagtccagct tggagcgaac tgcctacccg gaactgagtg tcaggcgtgg    4380
aatgagacaa acgcggccat aacagcgaaa tgacaccggt aaaccgaaag caggaacag    4440 gagagcgcac gagggagccg ccaggggaaa cgcctggtat ctttatagtc ctgtcgggtt    4500
tcgccaccac tgatttgagc gtcagatttc gtgatgcttg tcaggggggc ggagcctatg    4560
gaaaaacggc tttgccgcgg ccctctcact tccctgttaa gtatcttcct ggcatcttcc    4620
aggaaatctc cgccccgttc gtaagccatt tccgctcgcc gcagtcgaac gaccgagcgt    4680
agcgagtcag tgagcgagga agcggaatat atcctgtatc acatattctg ctgacgcacc    4740
ggtgcagcct ttttctcct gccacatgaa gcacttcact gacaccctca tcagtgccaa    4800
```

```
catagtaagc cagtatacac tccgctagcg ctgatgtccg gcggtgcttt tgccgttacg    4860
caccaccccg tcagtagctg aacaggaggg acagctgata gaaacagaag ccactggagc    4920
acctcaaaaa caccatcata cactaaatca gtaagttggc agcatacccc gacgcacttt    4980
gcgccgaata aatacctgtg acggaagatc acttcgcaga ataaataaat cctggtgtcc    5040
ctgttgatac cgggaagccc tgggccaact tttggcgaaa atgagacgtt gatcggcacg    5100
taagaggttc aactttcac cataatgaaa taagatcact accgggcgta ttttttgagt    5160
tatcgagatt ttcaggagct aaggaagcta aatggagaa aaaaatcact ggatatacca    5220
ccgttgatat atcccaatgg catcgtaaag aacattttga ggcatttcag tcagttgctc    5280
aatgtaccta taaccagacc gttcagctgg atattacggc cttttttaaag accgtaaaga    5340 aaaataagca caagttttat ccggcccttta ttcacattct gcccgcctg atgaatgctc    5400 atccggaatt t                                                         5411
```

<210> SEQ ID NO 18
<211> LENGTH: 284
<212> TYPE: PRT
<213> ORGANISM: Streptomyces murayamaensis

<400> SEQUENCE: 18

```
Met Leu Thr His Ser Phe Ala Arg Lys Leu Arg Leu Arg Arg Leu His
1               5                   10                  15

Arg His Gly Gly Glu Arg Leu Leu Ile Val Pro Leu Asp His Ser Ile
            20                  25                  30

Thr Asp Gly Pro Val Thr Gly Gly Asn Arg Leu Asp His Leu Val Gly
        35                  40                  45

Gln Leu Ala Val Asn Gly Val Asp Ala Val Leu His Lys Gly Ser
    50                  55                  60

Leu Arg Tyr Val Asp Ser Ala Arg Phe Ala Arg Thr Ser Leu Ile Val
65                  70                  75                  80

His Leu Ser Ala Ser Thr Val His Ala Pro Asp Pro Asp Glu Lys Tyr
                85                  90                  95

Leu Val Ala Ser Val Glu Glu Cys Leu Arg Leu Gly Ala Asp Ala Val
            100                 105                 110

Ser Val His Val Asn Leu Gly Ser Ala Gln Glu Arg Gln Gln Ile Ala
        115                 120                 125

Asp Leu Ala Ala Val Gly Asp Ala Cys Asp Arg Trp Asn Val Pro Leu
    130                 135                 140

Leu Ala Met Met Tyr Pro Arg Gly Pro Lys Ile Thr Asn Pro Arg Asp
145                 150                 155                 160

Pro Ala Leu Ile Ala His Ala Ala Ser Leu Ala Ala Asp Leu Gly Ala
                165                 170                 175

Asp Ile Val Lys Thr Val Cys Ala Glu Thr Ile Gly Glu Met Arg Asp
            180                 185                 190

Ile Thr Ser Ala Ser Pro Val Pro Leu Val Val Gly Gly Pro Arg
        195                 200                 205

Glu Pro Asp Glu Lys Arg Val Leu Ala Tyr Val Asp Glu Ala Leu Arg
    210                 215                 220

Gly Gly Ala Ser Gly Val Ala Met Gly Arg Asn Val Phe Leu Ala Pro
225                 230                 235                 240

Asp Pro Gly Ala Met Ala Ala Lys Val Ser Arg Leu Ile His Pro Ala
                245                 250                 255

Val Arg Arg Glu Val Pro Thr Asp His Val Pro Ala Pro Asn Ala Pro
```

```
              260                 265                 270
Ala Asp Asp Arg Thr Ala Pro Leu Thr Thr Val Ser
            275                 280

<210> SEQ ID NO 19
<211> LENGTH: 855
<212> TYPE: DNA
<213> ORGANISM: Streptomyces murayamaensis

<400> SEQUENCE: 19
atgttgaccc attccttcgc ccggaagctg cggctgcggc ggctgcaccg ccacggcggc      60
gagcggctgc tgatcgtgcc gctcgaccac tcgatcaccg acggaccggt gaccggcggc     120
aaccggctcg accatctggt ggggcagctc gccgtcaacg cgtggacgc cgtggtgctg      180
cacaagggca gcctgcgcta tgtcgactcg gcccggttcg cccgtacgtc gctgatcgtg     240
catctgagcg ccagcaccgt gcacgccccc gacccggacg agaagtacct ggtcgccagc     300
gtcgaggagt gcctgcggct gggcgcggac gcggtcagct gcacgtcaa cctcggttcc      360
gcccaggagc gccagcagat cgcggacctg gcggcggtcg cgacgcctg cgaccgctgg      420
aacgttccgc tgctcgccat gatgtatccg cgcggtccga agatcaccaa ccccgtgac      480
ccggcgctga tcgcccacgc ggcctcgctc gccgccgacc tgggcgccga catcgtcaag     540
accgtctgcg ccgagaccat cggcgagatg cgggacatca ccagcgcctc ccccgtcccg     600
ctcgtcgtgg tcggcggccc ccgcgagccc gacgagaagc gcgtgctcgc ctacgtggac     660
gaggcgctgc gcggcggcgc gtccggtgtc gcgatgggcc gcaacgtctt cctcgcgccg     720
gaccccggcg ccatggccgc caaggtgtcc cgcctgatcc accccgccgt acggcgcgag     780
gtgccgaccg accatgtgcc ggcgcccaac gcacccgccg atgaccgcac cgccccgttg     840
accaccgtct cttaa                                                      855

<210> SEQ ID NO 20
<211> LENGTH: 367
<212> TYPE: PRT
<213> ORGANISM: Streptomyces murayamaensis

<400> SEQUENCE: 20

Met Lys Ile Ser Trp Leu Asp Ala Arg Ser Leu Gly Asp Ala Lys Glu
1               5                  10                  15

Ala Ile Leu Gln Glu Ala Leu His Tyr Arg Leu Glu Gly Ile Val Ala
              20                  25                  30

Glu Asp Pro Ala Asp Phe Ala Asp Leu Pro Pro Thr Leu Thr Lys Val
          35                  40                  45

Leu Leu Pro Arg Lys Glu Leu Pro Ala Glu Phe Gly Asp Ala Ser Val
      50                  55                  60

Val Ile Val Asp Pro Thr Val His Gly Val Thr Pro Ala Glu Leu Ala
65                  70                  75                  80

Leu Lys Tyr Pro Asp Ile Glu Phe Gly Arg Phe Val Glu Ile Ile Asp
              85                  90                  95

Ala Pro Thr Leu Glu Asp Ala Cys Glu Ser Ala Arg Thr Glu Lys Trp
         100                 105                 110

Ser Val Leu Leu Phe Arg Asp Pro Thr Lys Ile Pro Leu Glu Ile Val
         115                 120                 125

Ile Ala Ala Ala Arg Ala Lys Gly Ser Met Ile Thr Val Ala Lys
     130                 135                 140

Asp Val Glu Glu Ala Glu Ile Ile Phe Gly Val Leu Glu His Gly Ser
```

145                 150                 155                 160
Asp Gly Val Met Met Ala Pro Ala Ala Val Gly Asp Ala Ala Lys Leu
                165                 170                 175

Lys Ala Ala Thr Ala Asp Val Pro Asp Leu Asp Leu Val Glu Leu
                180                 185                 190

Thr Val Glu Lys Thr Glu His Ile Gly Met Gly Glu Arg Ala Cys Val
                195                 200                 205

Asp Thr Cys Thr Tyr Phe Arg Glu Asp Glu Gly Ile Leu Val Gly Ser
        210                 215                 220

His Ser Lys Gly Met Val Leu Cys Val Ser Glu Thr His Pro Leu Pro
225                 230                 235                 240

Tyr Met Pro Thr Arg Pro Phe Arg Val Asn Ala Gly Ala Ile His Ser
                245                 250                 255

Tyr Thr Leu Ser Lys Asp Glu Arg Thr Asn Tyr Leu Ser Glu Leu Lys
                260                 265                 270

Ala Gly Ser Lys Val Leu Ala Val Asp Ile Lys Gly Gln Thr Arg Leu
            275                 280                 285

Val Thr Val Gly Arg Val Lys Ile Glu Ser Arg Pro Leu Ile Ser Ile
        290                 295                 300

Asp Ala Val Ala Pro Asn Gly Gln Arg Val Asn Leu Ile Leu Gln Asp
305                 310                 315                 320

Asp Trp His Val Arg Val Leu Gly Pro Gly Gly Val Val Leu Asn Ser
                325                 330                 335

Thr Glu Leu Lys Pro Gly Asp Thr Val Leu Gly Phe Leu Pro Ser Glu
                340                 345                 350

Asp Arg His Val Gly Tyr Pro Ile Asp Glu Phe Cys Leu Glu Lys
                355                 360                 365

<210> SEQ ID NO 21
<211> LENGTH: 1104
<212> TYPE: DNA
<213> ORGANISM: Streptomyces murayamaensis

<400> SEQUENCE: 21
atgaagatca gctggctcga cgcccgttcg ctcggcgacg ccaaggaggc catcctccag      60
gaggccctgc actaccgcct ggaaggcatc gtcgccgagg accccgccga cttcgccgac    120
ctgccgccga ccctcaccaa ggtgctgctg ccgcgcaagg agctgcccgc cgagttcggc    180
gacgcctccg tggtcatcgt ggacccgacc gtgcacggcg tgaccccggc cgaactcgcc    240
ctgaagtacc cggacatcga gttcggccgc ttcgtggaga tcatcgacgc gcccaccctt    300
gaggacgcct gcgagtcggc gcgcaccgag aagtggagcg tgctgctctt ccgcgacccc    360
accaagatcc cgctggagat cgtgatcgcg cggccgcccc gcgccaaggg cagcatgatc    420
acggtggcca aggacgtgga ggaggccgag atcatcttcg gcgtcctgga gcacggctcg    480
gacggcgtga tgatggcgcc ggcggcggtc ggcgacgcgg ccaagctgaa ggccgccgcc    540
accgccgacg tgcccgacct cgacctcgtc gagctcaccg tcgagaagac cgagcacatc    600
ggcatgggcg agcgcgcctg cgtcgacacc tgcacgtact ccgcgaggga cgagggcatc    660
ctggtcggct cgcactccaa gggcatggtc ctgtgcgtca gcgagacgca cccgctgccg    720
tacatgccga cccggccgtt ccgggtcaac gcgggcgcga tccactcgta cacgctctcc    780
aaggacgagc ggaccaacta cctcagcgag ctgaaggcgg cagcaaggt gctggccgtc    840 gacatcaagg ggcagacgcg gctggtcacc gtcgggcggg tcaagatcga gtcccggccg    900

```
ctgatctcga tcgacgcggt ggcgccgaac gggcagcggg tgaatctgat tcttcaggac      960
gactggcacg tgcgggtgct cggcccgggg ggtgtcgtgc tcaacagcac cgagctgaag     1020
ccgggggaca ccgttctggg gttcctgccc agcgaggacc ggcatgtcgg ttacccgatc     1080
gatgagttct gcctggagaa gtag                                            1104

<210> SEQ ID NO 22
<211> LENGTH: 4937
<212> TYPE: DNA
<213> ORGANISM: Artificial Sequence
<220> FEATURE:
<223> OTHER INFORMATION: Nucleotide sequence of pMW219-nhoA

<400> SEQUENCE: 22
aattcttgaa gacgaaaggg cctcgtgata cgcctatttt tataggttaa tgtcatgata       60
ataatggttt cttagacgtc aggtggcact tttcggggaa atgtgcgcgg aacccctatt      120
tgtttatttt tctaaataca ttcaaatatg tatccgctca tgagacaata accctgataa      180
atgcttcaat aatattgaaa aaggaagagt atgagtattc aacatttccg tgtcgccctt      240
attccctttt ttgcggcatt ttgccttcct gttttgctc acccagaaac gctggtgaaa       300
gtaaaagatg ctgaagatca gttgggtgca cgagtgggt acatcgaact ggatctcaac      360
agcggtaaga tccttgagag ttttcgcccc gaagaacgct catgtttgac agcttatcat      420
cgatatgctt aatgcggta gtgatcaaga gacaggatga ggatcgtttc gcatgattga       480
acaagatgga ttgcacgcag gttctccggc cgcttgggtg gagaggctat tcggctatga      540
ctgggcacaa cagacaatcg gctgctctga tgccgccgtg ttccggctgt cagcgcaggg      600
gcgcccggtt ctttttgtca agaccgacct gtccggtgcc ctgaatgaac tgcaggacga      660
ggcagcgcgg ctatcgtggc tggccacgac gggcgttcct tgcgcagctg tgctcgacgt      720
tggcactgaa gcgggaaggg actggctgct attgggcgaa gtgccggggc aggatctcct      780
gtcatctcac cttgctcctg ccgagaaagt atccatcatg gctgatgcaa tgcggcggct      840
gcatacgctt gatccggcta cctgcccatt cgaccaccaa gcgaaacatc gcatcgagcg      900
agcacgtact cggatggaag ccggtcttgt cgatcaggat gatctggacg aagagcatca      960
ggggctcgcg ccagccgaac tgttcgccag gctcaaggcg cgcatgcccg acggcgagga     1020
tctcgtcgtg acccatggcg atgcctgctt gccgaatatc atggtggaaa atggccgctt     1080
ttctggattc atcgactgtg gccggctggg tgtggcggac cgctatcagg acatagcgtt     1140
ggctacccgt gatattgctg aagagcttgg cggcgaatgg gctgaccgct tcctcgtgct     1200
ttacggtatc gccgctcccg attcgcagcg catcgccttc tatcgccttc ttgacgagtt     1260
cttctgagcg ggactctggg gttcggcaca cagcccagct tggagcgaac gacctacacc     1320
gaactgagat acctacagcg tgagctatga gaaagcgccc aatacgcaaa ccgcctctcc     1380
ccgcgcgttg gccgattcat taatgcagct ggcacgacag gtttcccgac tggaaagcgg     1440
gcagtgagcg caacgcaatt aatgtgagtt agctcactca ttaggcaccc caggctttac     1500
actttatgct tccggctcgt atgttgtgtg gaattgtgag cggataacaa tttcacacag     1560
gaaacagcta tgaccatgat tacgccaagc ttgtgagcga agaaggtttt tttaagcgta     1620
gtccgtaacg caataagtaa cgaaattaac gggattggcg atttgcgaac gtgatgcatg     1680
tccgcgatcg cacaaaatag ccggtgcggc gtctattcca ggttataagt tgagaaaacc     1740
actaagggaa acgcctgatg acgcccattc tgaatcacta ttttgcccgt attaactggt     1800
cgggagctgc tgcggtcaat attgatacgc ttcgtgcatt gcacctgaaa cacaattgca     1860
```

```
ccattccgtt tgaaaacctc gacgttttgc tgccgaggga aatacagctt gataatcaat    1920
cgccggaaga gaaactggtg atagcccgtc gtggcggtta ctgttttgag cagaatggcg    1980
tgtttgagcg ggtgttacgc gagctggggt ttaacgttcg cagcttgtta gggcgcgtag    2040
tgttatcaaa tccgccagca ttaccgccgc gcacccatcg tttgctgttg gtggaactgg    2100
aagaggaaaa atggattgct gatgtcggtt tcggtgggca gacgctaacc gcgccgattc    2160
gtttagtttc cgatctcgtg cagaccacgc cacacggaga gtatcggttg ttgcaggagg    2220
gtgatgattg ggtgttgcag tttaatcatc atcagcattg cagtcgatg taccgttttg     2280
atctctgcga gcagcaacaa agcgattatg tgatgggcaa tttctggtcg gcgcactggc    2340
cgcagtcgca ttttcgccat catttgctga tgtgccgcca tttgccggac ggcggcaagc    2400
tgacactgac caattttcat tttacccatt atgaaaatgg gcacgcggtg gagcagcgaa    2460
atctaccgga tgtggcgtca ttatatgctg tgatgcaaga acagtttggt ctgggcgtgg    2520
atgatgcgaa acatggcttt accgtggatg agttagcgct ggtgatggcg gcgtttgata    2580
cgcacccgga ggcgggaaaa taatttatgt caggttgccg gatgcggcgt aaacgcctta    2640
tccggcatac agaattcact ggccgtcgtt ttacaacgtc gtgactggga aaaccctggc    2700
gttacccaac ttaatcgcct tgcagcacat ccccctttcg ccagctggcg taatagcgaa    2760
gaggcccgca ccgatcgccc ttcccaacag ttgcgcagcc tgaatggcga atggcgctat    2820
ttcttccaga attgccatga tttttttccc acgggaggcg tcactggctc ccgtgttgtc    2880
ggcagctttg attcgataag cagcatcgcc tgtttcaggc tgtctatgtg tgactgttga    2940
gctgtaacaa gttgtctcag gtgttcaatt tcatgttcta gttgctttgt tttactggtt    3000
tcacctgttc tattaggtgt tacatgctgt tcatctgtta cattgtcgat ctgttcatgg    3060
tgaacagctt tgaatgcacc aaaaactcgt aaaagctctg atgtatctat cttttttaca    3120
ccgttttcat ctgtgcatat ggacagtttt ccctttgata tgtaacggtg aacagttgtt    3180
ctacttttgt ttgttagtct tgatgcttca ctgatagata caagagccat aagaacctca    3240
gatccttccg tatttagcca gtatgttctc tagtgtggtt cgttgttttt gcgtgagcca    3300
tgagaacgaa ccattgagat catgcttact ttgcatgtca ctcaaaaatt ttgcctcaaa    3360
actggtgagc tgaattttg cagttaaagc atcgtgtagt gtttttctta gtccgttatg     3420
taggtaggaa tctgatgtaa tggttgttgg tattttgtca ccattcattt ttatctggtt    3480
gttctcaagt tcggttacga gatccatttg tctatctagt tcaacttgga aaatcaacgt    3540
atcagtcggg cggcctcgct tatcaaccac caatttcata ttgctgtaag tgtttaaatc    3600
tttacttatt ggtttcaaaa cccattggtt aagccttta aactcatggt agttatttc      3660
aagcattaac atgaacttaa attcatcaag gctaatctct atatttgcct tgtgagtttt    3720
cttttgtgtt agttctttta ataaccactc ataaatcctc atagagtatt tgttttcaaa    3780
agacttaaca tgttccagat tatattttat gaattttttt aactgaaaaa gataaggcaa    3840
tatctcttca ctaaaaacta attctaattt ttcgcttgag aacttggcat agtttgtcca    3900
ctggaaaatc tcaaagcctt taaccaaagg attcctgatt tccacagttc tcgtcatcag    3960
ctctctggtt gctttagcta atacaccata agcattttcc ctactgatgt tcatcatctg    4020
agcgtattgg ttataagtga acgataccgt ccgttctttc cttgtagggt tttcaatcgt    4080
ggggttgagt agtgccacac agcataaaat tagcttggtt tcatgctccg ttaagtcata    4140
gcgactaatc gctagttcat ttgctttgaa aacaactaat tcagacatac atctcaattg    4200
```

-continued

```
gtctaggtga ttttaatcac tataccaatt gagatgggct agtcaatgat aattactagt      4260
ccttttcctt tgagttgtgg gtatctgtaa attctgctag acctttgctg gaaaacttgt      4320
aaattctgct agaccctctg taaattccgc tagacctttg tgtgtttttt ttgtttatat      4380
tcaagtggtt ataatttata gaataaagaa agaataaaaa aagataaaaa gaatagatcc      4440
cagccctgtg tataactcac tactttagtc agttccgcag tattacaaaa ggatgtcgca      4500
aacgctgttt gctcctctac aaaacagacc ttaaaacccct aaaggcttaa gtagcaccct      4560
cgcaagctcg ggcaaatcgc tgaatattcc ttttgtctcc gaccatcagg cacctgagtc      4620
gctgtctttt tcgtgacatt cagttcgctg cgctcacggc tctggcagtg aatggggta      4680 aatggcacta caggcgcctt ttatggattc atgcaaggaa actacccata atacaagaaa      4740
agcccgtcac gggcttctca gggcgtttta tggcgggtct gctatgtggt gctatctgac      4800
tttttgctgt tctgcagttc ctgccctctg attttccagt ctgaccactt cggattatcc      4860
cgtgacaggt cattcagact ggctaatgca cccagtaagg cagcggtatc atcaacaggc      4920
ttacccgtct tactgtc                                                     4937
```

<210> SEQ ID NO 23
<211> LENGTH: 7693
<212> TYPE: DNA
<213> ORGANISM: Artificial Sequence
<220> FEATURE:
<223> OTHER INFORMATION: Nucleotide sequence of pVC7-nhoA

<400> SEQUENCE: 23

```
agcttgtcta cgtctgatgc tttgaatcgg acggacttgc cgatcttgta tgcggtgatt       60
tttccctcgt ttgcccactt tttaatggtg gccggggtga gagctacgcg ggcggcgacc      120
tgctgcgctg tgatccaata ttcggggtcg ttcactggtt cccctttctg atttctggca      180
tagaagaacc cccgtgaact gtgtggttcc gggggttgct gattttgttc ggaggacttc      240
tcgcgcaatt ccctagctta ggtgaaaaca ccatgaaaca ctagggaaac acccatgaaa      300
cacccattag ggcagtaggg cggcttcttc gtctagggct tgcatttggg cggtgatctg      360
gtctttagcg tgtgaaagtg tgtcgtaggt ggcgtgctca atgcactcga acgtcacgtc      420
atttaccggg tcacggtggg caaagagaac tagtgggtta gacattgttt tcctcgttgt      480
cggtggtggt gagcttttct agccgctcgg taaacgcggc gatcatgaac tcttggaggt      540
tttcaccgtt ctgcatgcct gcgcgcttca tgtcctcacg tagtgccaaa ggaacgcgtg      600
cggtgaccac gacgggctta gccttttgcct gcgcttctag tgcttcgatg gtggcttgtg      660
cctgcgcttg ctgcgcctgt agtgcctgtt gagcttcttg tagttgctgt tctagctgtg      720
ccttggttgc catgctttaa gactctagta gcttttcctgc gatatgtcat gcgcatgcgt      780
agcaaacatt gtcctgcaac tcattcatta tgtgcagtgc tcctgttact agtcgtacat      840
actcatattt acctagtctg catgcagtgc atgcacatgc agtcatgtcg tgctaatgtg      900
taaaacatgt acatgcagat tgctgggggt gcaggggcg gacgacctgg tccatgcggg      960
gtgtggggct tgcgcggtac agacagtgag caccggggca cctagtcgcg gataccccc      1020 ctaggtatcg gacacgtaac cctcccatgt cgatgcaaat cttttaacatt gagtacgggt      1080 aagctggcac gcatagccaa gctaggcggc caccaaacac cactaaaaat taatagttcc      1140
ctagacaaga caaaccccg tgcgagctac caactcatat gcacggggc cacataaccc      1200 gaagggggttt caattgacaa ccatagcact agctaagaca acgggcacaa cacccgcaca      1260
aactcgcact gcgcaacccc gcacaacatc gggtctaggt aacactgaaa tagaagtgaa      1320
```

```
cacctctaag gaaccgcagg tcaatgaggg ttctaaggtc actcgcgcta gggcgtggcg   1380
taggcaaaac gtcatgtaca agatcaccaa tagtaaggct ctggcggggt gccataggtg   1440
gcgcagggac gaagctgttg cggtgtcctg gtcgtctaac ggtcgttcgc agtttgaggg   1500
tctgcaaaac tctcactctc gctggggtc acctctggct gaattggaag tcatgggcga    1560
acgccgcatt gagctggcta ttgctactaa gaatcacttg gcggcgggtg gcgcgctcat   1620
gatgtttgtg ggcactgttc gacacaaccg ctcacagtca tttgcgcagg ttgagagctg   1680
ggtattaaga ctgcgtactc ttcgatggtg aaaacatctc agtggaagaa agaacgtgca   1740
cggtacgggg tggagcacac ctatagtgac tatgaggtca cagactcttg ggcgaacggt   1800
tggcacttgc accgcacatg ctgttgttct tggatcgtcc actgtctgac gatgaactca   1860
aggcgtttga ggattccatg ttttcccgct ggtctgctgg tgtggttaag gccggtatgg   1920
acgcgccact gcgtgagcac ggggtcaaac ttgatcaggt gtctacctgg ggtggagacg   1980
ctgcgaaaat ggcaacctac ctcgctaagg gcatgtctca ggaactgact ggctccgcta   2040
ctaaaaccgc gtctaagggg tcgtacacgc cgtttcagat gttggatatg ttggccgatc   2100
aaagcgacgc cggcgaggat atggacgctg ttttggtggc tcggtggcgt gagtatgagg   2160
ttggttctaa aaacctgcgt tcgtcctggt cacgtggggc taagcgtgct ttgggcattg   2220
attacataga cgctgatgta cgtcgtgaaa tggaagaaga actgtacaag ctcgccggtc   2280
tggaagcacc ggaacgggtc gaatcaaccc gcgttgctgt tgctttggtg aagcccgatg   2340
attggaaact gattcagtct gatttcgcgg ttaggcagta cgttctagat tgcgtggata   2400
aggctaagga cgtggccgct cgcaacgtg tcgctaatga ggtgctggca agtctgggtg     2460
tggattccac cccgtgcatg atcgttatgg atgatgtgga cttggacgcg ttctgccta    2520 ctcatgggga cgctactaag cgtgatctga atgcggcggt gttcgcgggt aatgagcaga   2580
ctattcttcg cacccactaa aagcggcata aaccccgttc gatattttgt gcgatgaatt   2640
tatggtcaat gtcgcggggg caaactatga tgggtcttgt tgttgacaat ggctgatttc   2700
atcaggaatg gaactgtcat gctgttatgt gcctggctcc taatcaaagc tggggacaat   2760
gggttgcccc gttgatctga tctagttcgg attggcgggg cttcactgta tctgggggtg   2820
gcatcgtgaa tagattgcac accgtagtgg gcagtgtgca caccatagtg ggcatgagta   2880
atacctacgc gcggctgggc tagggcttaa cgcgcttttg ccgtgctgcg gggcatacgt   2940
tagcgcatac gcttttttct gtgaaacctt tttgtgttgt tgtttcgtgt tggtttcctt   3000
tctgttggcg gggcaactta acgctgcggg ggtggttgtt gacgttaacg ggggtagttt   3060
ttattcccct agtggttttt cagtacgaca atcgagaaag acctgtttca gccagttcgg   3120
gtcatgttcg tcggtatggc cacgtgcata gcgaccagtt ttcgagttca ctgggatttt   3180
tggtgcatcg aacaagatgt aggacaatgc ggtttctagg tctactttt gctttatgcc    3240 gtacaagccc cgtgggtatt cagcgattga ttccaaggcg gcttcccagt cctgttttgt   3300
gaaggactgg cttagttcta ggtctgtgtc tgggtagtac tgcttgtttg tgtaagcgcc   3360
gttggtgctc attgatgatt cctttgaagt gtttggagtt cggctagtag tgcggcgtat   3420
ggtgctgctt tttgctcgtg atagctcgcc ttggctatga ggtcggctag gtaggtttcc   3480
ggggtgccta ggttgcgtag gtctagcaaa tcccggtatg tggcctgtgc gctgcgctgg   3540
tggtgcatac agtcgttaag ctgggcttttt acgtctgcga tgcggtggcg gttaggcatg   3600
ttggtgtgct tcttccaagt actcacgggc gggttttgtg tatgcctggc gtgatgcttc   3660
```

| | |
|---|---:|
| tttgagctgt tggagttccg cttcggagtg cgggtagttc gtccgcgaac tgcttgtggt | 3720 |
| actcgtattt ctcttgttcc tgggcgatca gatttgcgtt gaattgcagg gcggtgagtt | 3780 |
| cgtccacgcg tcgttttgct gcgttggtca tggtggcgtg ccatttgcgg ttgtggacgc | 3840 |
| ggggttcaag gttgcgcacg gctgcttcgg ctaggttggt ggctgctttt ttcagtgctc | 3900 |
| gggcttcccg ttcctcgtcc aacgagagca ccttttggtt tgttggcttc ggctagtttt | 3960 |
| tgcttctccg ctttgatgag ttggtcaact tcgtgttggg agaggtcgtt tttcacgatg | 4020 |
| cgtcgaatgt ggtcgttgtg ggtgctgagt tggtgtgaga ggtagtgggg ttctgggatt | 4080 |
| tcggcgagtt ggtcgaggtt ggtgtagtgc gggttgcggc ctggttggtt gggttcgctg | 4140 |
| gggaggtcga tgtatccggt tgagtctccg gcgtggttga agtgaattag gcgttggtag | 4200 |
| ccgtattcct ggttggggag gtacgacaga atgaggaagt ttggtgcttc tcctgcaatg | 4260 |
| agtcgtgcgt gttcgtagtt cggtactggg tcgtgctcgg ggagaatgtt cttttgggtc | 4320 |
| atggcttctc tttctgttgc tctgtaagtc cgtatgtggg catgggaaag ccccggcaac | 4380 |
| cctttgggtc aaccggggct agatagtcgc ttagaatggc ttctaggctg cgtctcgggg | 4440 |
| tgtgggcaag ctgtaagagg ttccaacttt caccataatg aaataagatc actaccgggc | 4500 |
| gtattttttg agttatcgag attttcagga gctaaggaag ctaaaatgga gaaaaaaatc | 4560 |
| actggatata ccaccgttga tatatcccaa tggcatcgta agaacatttt tgaggcattt | 4620 |
| cagtcagttg ctcaatgtac ctataaccag accgttcagc tggatattac ggccttttta | 4680 |
| aagaccgtaa agaaaaataa gcacaagttt tatccggcct ttattcacat tcttgcccgc | 4740 |
| ctgatgaatg ctcatccgga atttcgtatg gcaatgaaag acggtgagct ggtgatatgg | 4800 |
| gatagtgttc acccttgtta caccgttttc catgagcaaa ctgaaacgtt ttcatcgctc | 4860 |
| tggagtgaat accacgacga tttccggcag tttctacaca tatattcgca agatgtggcg | 4920 |
| tgttacggtg aaaacctggc ctatttccct aaagggttta ttgagaatat gttttttcgtc | 4980 |
| tcagccaatc cctgggtgag tttcaccagt tttgatttaa acgtggccaa tatggacaac | 5040 |
| ttcttcgccc ccgttttcac catgggcaaa tattatacgc aaggcgacaa ggtgctgatg | 5100 |
| ccgctggcga ttcaggttca tcatgccgtc tgtgatggct tccatgtcgg cagaatgctt | 5160 |
| aatgaattac aacagtactg cgatgagtgg cagggcgggg cgtaattttt ttaaggcagt | 5220 |
| tattggtgcc cttaaacgcc tggtgctacg cctgaataag tgataataag cggatgaatg | 5280 |
| gcagaaattc agcttggccc agtgccaagc tccaatacgc aaaccgcctc tccccgcgcg | 5340 |
| ttggccgatt cattaatgca gctggcacga caggttttcccc gactgaaaag cgggcagtga | 5400 |
| gcgcaacgca attaatgtga gttagctcac tcattaggca ccccaggctt tacactttat | 5460 |
| gcttccggct cgtatgttgt gtggaattgt gagcggataa caatttcaca caggaaacag | 5520 |
| ctatgaccat gattacgcca agcttgtgag cgaagaaggt ttttttaagc gtagtccgta | 5580 |
| acgcaataag taacgaaatt aacgggattg gcgatttgcg aacgtgatgc atgtccgcga | 5640 |
| tcgcacaaaa tagccggtgc ggcgtctatt ccaggttata agttgagaaa accactaagg | 5700 |
| gaaacgcctg atgacgccca ttctgaatca ctattttgcc cgtattaact ggtcgggagc | 5760 |
| tgctgcggtc aatattgata cgcttcgtgc attgcacctg aaacacaatt gcaccattcc | 5820 |
| gtttgaaaac ctcgacgttt tgctgccgag ggaaatacag cttgataatc aatcgccgga | 5880 |
| agagaaactg gtgatagccc gtcgtggcg ttactgtttt gagcagaatg gcgtgtttga | 5940 |
| gcgggtgtta cgcgagctgg ggtttaacgt tcgcagcttg ttagggcgcg tagtgttatc | 6000 |
| aaatccgcca gcattaccgc cgcgcaccca tcgtttgctg ttggtggaac tggaagagga | 6060 |

-continued

```
aaaatggatt gctgatgtcg gtttcggtgg gcagacgcta accgcgccga ttcgtttagt   6120
ttccgatctc gtgcagacca cgccacacgg agagtatcgg ttgttgcagg agggtgatga   6180
ttgggtgttg cagtttaatc atcatcagca ttggcagtcg atgtaccgtt ttgatctctg   6240
cgagcagcaa caaagcgatt atgtgatggg caatttctgg tcggcgcact ggccgcagtc   6300
gcattttcgc catcatttgc tgatgtgccg ccatttgccg gacggcggca agctgacact   6360
gaccaatttt cattttaccc attatgaaaa tgggcacgcg gtggagcagc gaaatctacc   6420
ggatgtggcg tcattatatg ctgtgatgca agaacagttt ggtctgggcg tggatgatgc   6480
gaaacatggc tttaccgtgg atgagttagc gctggtgatg gcggcgtttg atacgcaccc   6540
ggaggcggga aaataattta tgtcaggttg ccggatgcgg cgtaaacgcc ttatccggca   6600
tacagaattc actggccgtc gttttacaac gtcgtgactg ggaaaaccct ggcgttaccc   6660
aacttaatcg ccttgcagca catccccctt tcgccagctg gcgtaatagc gaagaggccc   6720
gcaccgatcg cccttcccaa cagttgcgca gcctgaatgg cgaatgagct tcttccgctt   6780
cctcgctcac tgactcgctg cgctcggtcg ttcggctgcg gcgagcggta tcagctcact   6840
caaaggcggt aatacggtta tccacagaat caggggataa cgcaggaaag aacatgtgag   6900
caaaaggcca gcaaaaggcc aggaaccgta aaaaggccgc gttgctggcg ttttttccata   6960
ggctccgccc ccctgacgag catcacaaaa atcgacgctc aagtcagagg tggcgaaacc   7020
cgacaggact ataaagatac caggcgtttc ccctggaag ctccctcgtg cgctctcctg    7080
ttccgaccct gccgcttacc ggatacctgt ccgcctttct cccttcggga agcgtggcgc   7140
tttctcaatg ctcacgctgt aggtatctca gttcggtgta ggtcgttcgc tccaagctgg   7200
gctgtgtgca cgaaccccccc gttcagcccg accgctgcgc cttatccggt aactatcgtc   7260
ttgagtccaa cccggtaaga cacgacttat cgccactggc agcagccact ggtaacagga   7320
ttagcagagc gaggtatgta ggcggtgcta cagagttctt gaagtggtgg cctaactacg   7380
gctacactag aaggacagta tttggtatct gcgctctgct gaagccagtt accttcggaa   7440
aaagagttgg tagctcttga tccggcaaac aaaccaccgc tggtagcggt ggtttttttg   7500
tttgcaagca gcagattacg cgcagaaaaa aaggatctca agaagatcct ttgatctttt   7560
ctacggggtc tgacgctcag tggaactccg tcgaacggaa gatcacttcg cagaataaat   7620
aaatcctggt gtccctgttg ataccgggaa gccctgggcc aacttttggc gaaaatgaga   7680
cgttgatcgg cac                                                      7693
```

METHOD FOR PRODUCING 3-ACETYLAMINO-4-HYDROXYBENZOIC ACID

CROSS-REFERENCE TO RELATED APPLICATION

This application is a continuation of, and claims priority under 35 U.S.C. §120 to, International Patent Application No. PCT/JP2013/056025, filed on Mar. 5, 2013, which claims priority therethrough under 35 U.S.C. §119 to Japanese Patent Application No. 2012-122388, filed on May 29, 2012, which are incorporated in their entireties by reference. Also, the Sequence Listing filed electronically herewith is hereby incorporated by reference (File name: 2014-11-19T_US-526_Seq_List; File size: 67 KB; Date recorded: Nov. 19, 2014).

BACKGROUND OF THE INVENTION

1. Field of the Invention

The present invention relates to a method for producing 3-acetylamino-4-hydroxybenzoic acid, and the like.

2. Brief Description of the Related Art

Amino-hydroxybenzoic acid-type compounds are useful as intermediates of dyes, agricultural chemicals, pharmaceuticals, and other organic synthesized products and as a monomer for polymer polybenzoxazole with high performance and heat resistance. 3-Amino-4-hydroxybenzoic acid (3,4-AHBA) is biosynthesized in two steps by both GriI and GriH. GriI catalyzes a carbon-carbon binding reaction between a C4 compound having an amino group and a C3 or C4 compound and GriH catalyzes cyclization of a C7 compound or cyclization of a C8 compound with decarboxylation using dihydroxyacetone phosphate (DHAP) and aspartate semialdehyde (ASA) as substrates.

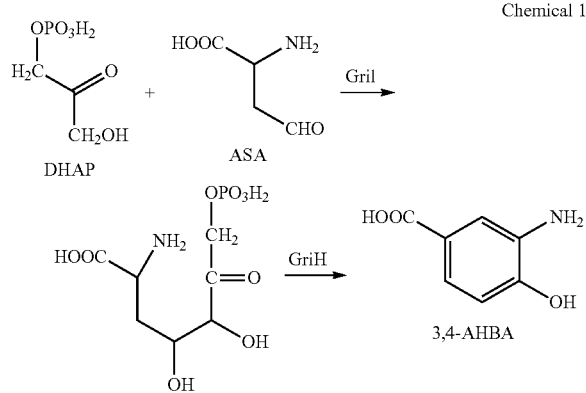

Chemical 1

3,4-AHBA is unstable, and easily oxidized to form 2-aminophenoxazin-3-one-8-carboxylic acid (APOC) (see below). JP 2004-283163-A describes that when 3,4-AHBA forms as a byproduct, it is converted into APOC over time in the culture medium during production of 3-acetylamino-4-hydroxybenzoic acid (3,4-AcAHBA). However, 3,4-AcAHBA is more stable than 3,4-AHBA because 3,4-AcAHBA is stabilized by acetylation and hence avoids oxidation. 3,4-AcAHBA can easily be converted into 3,4-AHBA by treating with an acid, a base or the like. 3,4-AcAHBA can be handled more easily than 3,4-AHBA that is oxidized to form APOC and thus is unstable. Therefore, development of an excellent method for producing 3,4-AcAHBA is desirable.

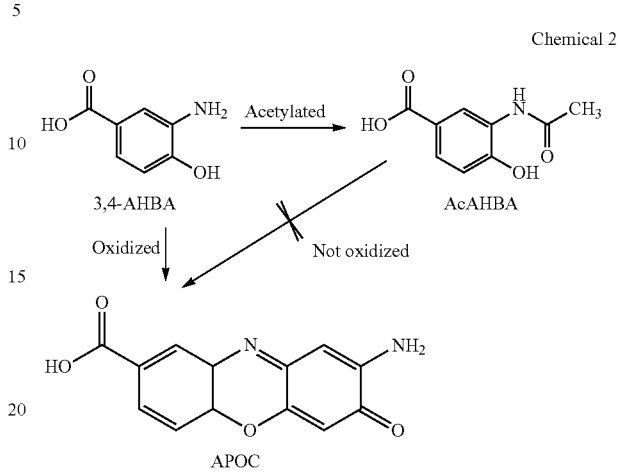

Chemical 2

JP 2004-283163-A describes that when 3,4-AHBA forms as a byproduct, it is converted into APOC over time in the culture medium during production of 3,4-AcAHBA. JP 2004-283163-A also discloses that 3,4-AcAHBA is deacetylated to form 3,4-AHBA.

International Publication WO2010/005099 discloses that 3,4-AHBA is formed by using *Corynebacterium glutamicum* that has been transformed with griI and griH.

J. Biol. Chem. 281 (2006), 36944-36951 discloses that 3,4-AHBA and 3,4-AcAHBA are formed by introducing griI and griH into *Escherichia coli*.

J. Bacteriol. 189 (2007), 2155-2159 discloses that 3,4-AcAHBA is not formed in culture by deleting arylamine N-acetyltransferase (natA) gene in *Streptomyces griseus*.

Biochim. Biophys. Acta. 1475 (2000), 10-16 discloses that N-hydroxyarylamine O-acetyltransferase (nhoA) gene derived from *Escherichia coli* works to catalyze acetylation for an aromatic amino group. Meanwhile, J. Antibiot., vol. 59 (2006), p. 464 discloses that *E. coli* BAP1 strain forms an N-acetylated product (3,5-AcAHBA) as a byproduct of 3,5-AHBA (a structural isomer of 3,4-AHBA), and also discloses that it is conceivable that NhoA is not a major factor for N-acetylation of 3,5-AHBA because 3,4-AcAHBA is also formed as a byproduct in an NhoA gene-deleted strain (MAR1 strain) of *E. coli* BAP1.

SUMMARY OF INVENTION

It is an aspect of disclosed subject matter to provide a method for conveniently and efficiently producing a stable 3-acetylamino-4-hydroxybenzoic acid-type compound by a process using a microorganism.

It has been found that nhoA is involved in production of 3,4-AcAHBA as a byproduct from 3,4-AHBA in *Escherichia coli*. Also, AcAHBA can be formed without production of the byproduct AHBA by the use of a microorganism modified so as to increase an NhoA activity, and the like.

It is an aspect of the disclosed subject matter to provide a microorganism that is able to produce 3-amino-4-hydroxybenzoic acid, wherein said microorganism is modified so as to increase formation of 3-amino-4-hydroxybenzoic acid from dihydroxyacetone phosphate and aspartate semialdehyde, wherein the microorganism is modified so as to increase an N-hydroxyarylamine O-acetyltransferase (NhoA) activity.

It is a further aspect of the disclosed subject matter to provide the microorganism as described above, wherein NhoA is increased by transformation with a recombinant vector comprising a DNA encoding the NhoA.

It is a further aspect of the disclosed subject matter to provide the microorganism as described above, wherein the NhoA is a protein selected from the group consisting of:

(I) a protein comprising the amino acid sequence of SEQ ID NO:2;

(II) a protein comprising an amino acid sequence having one or several amino acid substitutions, deletions, insertions or additions in the amino acid sequence of SEQ ID NO:2 and having an N-hydroxyarylamine O-acetyltransferase activity; and (III) protein comprising an amino acid sequence having 70% or more identity to the amino acid sequence of SEQ ID NO:2 and having an N-hydroxyarylamine O-acetyltransferase activity.

It is a further aspect of the disclosed subject matter to provide the microorganism as described above, wherein the DNA encoding the NhoA is selected from the group consisting of:

(i) a DNA comprising the nucleotide sequence of SEQ ID NO:3;

(ii) a DNA that hybridizes under a stringent condition with the nucleotide sequence complementary to the nucleotide sequence of SEQ ID NO:3 and encodes a protein having an N-hydroxyarylamine O-acetyltransferase activity; and (iii) a DNA comprising a nucleotide sequence having 70% or more identity to the nucleotide sequence of SEQ ID NO:3 and encoding a protein having an N-hydroxyarylamine O-acetyltransferase activity.

It is a further aspect of the disclosed subject matter to provide the microorganism as described above, wherein the microorganism belongs to the genus *Escherichia*, the genus *Pantoea*, or the genus *Corynebacterium*.

It is a further aspect of the disclosed subject matter to provide the microorganism as described above, wherein the microorganism is *Escherichia coli, Pantoea ananatis*, or *Corynebacterium glutamicum*.

It is a further aspect of the disclosed subject matter to provide the microorganism as described above], wherein 3-amino-4-hydroxybenzoic acid is produced by transformation with a recombinant vector comprising a DNA encoding a protein having an activity to form the 3-amino-4-hydroxybenzoic acid from the dihydroxyacetone phosphate and the aspartate semialdehyde.

It is a further aspect of the disclosed subject matter to provide the microorganism as described above, wherein the proteins having the activity to form 3-amino-4-hydroxybenzoic acid are GriI and GriH.

It is a further aspect of the disclosed subject matter to provide the microorganism as described above, wherein the GriI is selected from the group consisting of:

(A) a protein comprising an amino acid sequence of SEQ ID NO:9 or SEQ ID NO:18;

(B) a protein comprising an amino acid sequence having one or several amino acid substitutions, deletions, insertions or additions in the amino acid sequence in (A) above and having an aldolase activity; and (C) a protein comprising an amino acid sequence having 70% or more identity to the amino acid sequence in (A) above and having an aldolase activity;

and wherein the GriH protein is selected from the group consisting of:

(D) a protein comprising an amino acid sequence of SEQ ID NO:11 or SEQ ID NO:20;

(E) a protein comprising an amino acid sequence having one or several amino acid substitutions, deletions, insertions or additions in the amino acid sequence in (D) above and having a 3-amino-4-hydroxybenzoic acid synthase activity; and (F) a protein comprising an amino acid sequence having 70% or more identity to the amino acid sequence in (D) above and having a 3-amino-4-hydroxybenzoic acid synthase activity.

It is a further aspect of the disclosed subject matter to provide the microorganism as described above, wherein the DNA encoding the protein having the activity to form 3-amino-4-hydroxybenzoic acid is selected from the group consisting of:

(a) a DNA comprising a nucleotide sequence of SEQ ID NO:10 or SEQ ID NO:19;

(b) a DNA that hybridizes under a stringent condition with a nucleotide sequence complementary to the nucleotide sequence in (a) above and encodes a protein having an aldolase activity;

(c) a DNA that has 70% or more identity to the nucleotide sequence in (a) above and encodes a protein having an aldolase activity;

and wherein the griH gene is a DNA selected from the group consisting of:

(d) a DNA comprising a nucleotide sequence of SEQ ID NO:12 or SEQ ID NO:21;

(e) a DNA that hybridizes under a stringent condition with a nucleotide sequence complementary to the nucleotide sequence in (d) above and encodes a protein having a 3-amino-4-hydroxybenzoic acid synthase activity; and (f) a DNA that has 70% or more identity to the nucleotide sequence in (d) above and encodes a protein having a 3-amino-4-hydroxybenzoic acid synthase activity.

It is another aspect of the disclosed subject matter to provide a method for producing a 3-acetylamino-4-hydroxybenzoic acid-type compound, comprising culturing the microorganism as described above to form the 3-acetylamino-4-hydroxybenzoic acid-type compound.

It is a further aspect of the disclosed subject matter to provide the method for producing a 3-amino-4-hydroxybenzoic acid-type compound, comprising:

(1) forming a 3-acetylamino-4-hydroxybenzoic acid-type compound as described above; and (2) deacetylating the 3-acetylamino-4-hydroxybenzoic acid-type compound to form the 3-amino-4-hydroxybenzoic acid-type compound.

It is a further aspect to provide a method for producing a polymer containing a 3-amino-4-hydroxybenzoic acid-type compound as a component, comprising:

(1') forming the 3-amino-4-hydroxybenzoic acid-type compound as described above; and (2') polymerizing the 3-amino-4-hydroxybenzoic acid-type compound to obtain a polymer containing the 3-amino-4-hydroxybenzoic acid-type compound as a component.

It is a further aspect to provide the method as described above, wherein the polymer is a polybenzoxazole polymer.

According to the described subject matter, it is possible to conveniently and efficiently produce a stable 3-acetylamino-4-hydroxybenzoic acid-type compound.

DETAILED DESCRIPTION

Figure 1A:
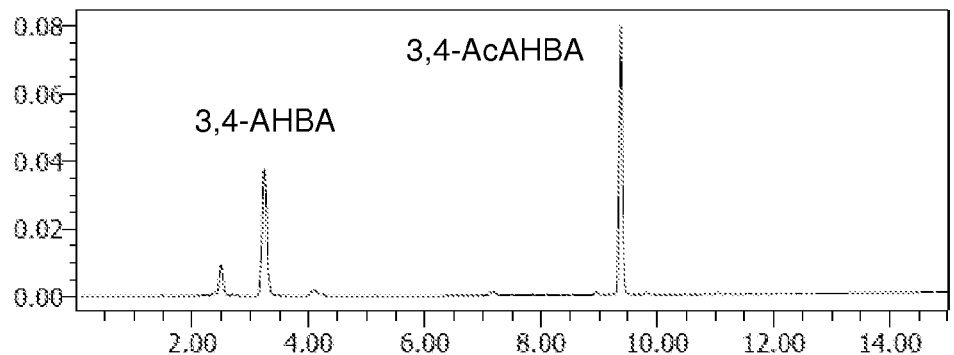
FIG. 1(*a*)-(*c*) show analysis results of (a) culture supernatant of *Escherichia coli* BW25113/pSTV28-EcGri/pUC19 strain, (b) culture supernatant of *Escherichia coli* BW25113/ pSTV28-EcGri/pUC19-NhoA strain, and (c) a 3,4-AHBA standard product, by reverse phase column chromatography.

The presently disclosed subject matter provides a microorganism having an ability to produce 3-acetylamino-4-hydroxybenzoic acid. When the microorganism is used, the formation of 3-acetylamino-4-hydroxybenzoic acid (3,4-AcAHBA) is facilitated, and accumulation of the non-acetylated product 3-amino-4-hydroxybenzoic acid (3,4-AHBA) can be suppressed in culture medium.

<1> Modification to Increase Activity of N-Hydroxyarylamine O-Acetyltransferase (NhoA)

The production of 3,4-AcAHBA can be facilitated by modifying a microorganism so as to increase the activity of N-hydroxyarylamine O-acetyltransferase (NhoA), and consequently accumulation of 3,4-AHBA can be suppressed in the culture medium. The NhoA activity is an N-hydroxyarylamine O-acetyltransferase activity, and refers to an activity to form 3-acetylamino-4-hydroxybenzoic acid (3,4-AcAHBA) from 3-amino-4-hydroxybenzoic acid (3,4-AHBA) in relationship with 3,4-AHBA.

"Modified so as to increase an NhoA activity" can mean that the NhoA activity becomes higher than the specific activity of an unmodified strain, e.g., a wild-type strain of the microorganism. The NhoA activity can be increased to 150% or more per microbial cell, 180% or more, or 200% or more per microbial cell, as compared with that of the unmodified strain. The microorganism as described herein has only to have more increased NhoA activity than the wild-type strain or the unmodified strain, but it is more desirable that the accumulation of 3,4-AcAHBA in the microorganism is enhanced compared with these strains. "Modified so as to increase an NhoA activity" can also corresponds to when a molecular number of NhoA per cell increases or when the NhoA activity per molecule increases, among others. Specifically, the modification to increase the NhoA activity may be introduced by ordinary mutagenesis or gene engineering treatment. Examples of the mutagenesis include X ray and ultraviolet ray irradiations, and treatments with mutagenic agents such as N-methyl-N'-nitro-N-nitrosoguanidine. Examples of such modification may include introduction of a mutation into a nhoA gene (including an expression regulating region) on a chromosome so that the NhoA activity can be increased compared with that of non-mutant strains. Such modification can be accomplished by transforming a desired microorganism with a recombinant vector including a DNA that encodes a protein having the NhoA activity.

The activity and the degree of an increase of the activity in a target enzyme can be confirmed by measuring the enzyme activity using a cell extract obtained from a candidate microbial strain or a purified fraction therefrom, and comparing it with an activity in the wild-type strain or the unmodified strain. For example, the NhoA activity can be measured by a method described in Biochim. Biophys. Acta. 1475 (2000), 10-16.

A microorganism modified so as to increase the NhoA activity can include a microorganism inherently able to produce 3,4-AHBA, and/or a microorganism to which the ability to produce 3,4-AHBA has been imparted. The ability to produce 3,4-AHBA can be imparted by methods described later. Examples of the microorganism may include, but are not limited to, bacteria, actinomycetes and fungi. The microorganisms can be bacteria belonging to the genus *Escherichia*, bacteria belonging to the genus *Pantoea*, or coryneform bacteria.

The bacteria belonging to the genus *Escherichia* that can be used include strains described in, for example, Neidhardt et al. (Neidhardt, F. C. Ed. 1996. Escherichia coli and Salmonella: Cellular and Molecular Biology/Second Edition pp. 2477-2483. Table 1. American Society for Microbiology Press, Washington, D.C.). Examples of *Escherichia coli* may include K12 strain (ATCC10798) or its substrains (e.g., BW25113(CGSC7630), DH1 (ATCC33747), MG1655 (ATCC700926), W3110(ATCC27325)), B strain or its substrains (e.g., BL21 (ATCC BAA-1025), REL606 (CGSC12149)) or the like. Those having a CGSC number in the above bacterial strains are available from The Coli Genetic Stock Center (cgsc.biology.yale.edu). Those having an ATCC number in the above bacterial strains are available from American Type Culture Collection (atcc.org).

Bacteria belonging to the genus *Pantoea* can mean bacteria classified into the genus *Pantoea* by professionals in microbiology. Some species of *Enterobacter agglomerans* have been recently reclassified into *Pantoea agglomerans*, *Pantoea ananatis*, *Pantoea stewartii*, and the like, based on analysis of nucleotide sequences of 16S rRNA and the like (Int. J. Syst. Bacteriol. 1993. 43: 162-173). In the present invention, the bacteria belonging to the genus *Pantoea* also include such bacteria reclassified into the genus *Pantoea*. Representative bacterial strains in the genus *Pantoea* may include *Pantoea ananatis*, *Pantoea stewartii*, *Pantoea agglomerans*, and *Pantoea citrea*. Specific examples thereof may include *Pantoea ananatis* AJ13355 strain (FERM BP-6614) (Europe Patent Application Publication No. 0952221), *Pantoea ananatis* AJ13356 strain (FERM BP-6615) (Europe Patent Application Publication No. 0952221), and the like. These bacterial strains are described as bacteria belonging to *Enterobacter agglomerans* in Europe Patent Application Publication No. 0952221, but have been currently reclassified into *Pantoea ananatis* based on the analysis of the nucleotide sequences of 16S rRNA and the like as described above.

The group of coryneform bacteria includes bacteria that were conventionally classified into the genus *Brevibacterium* but have been currently integrated into the genus *Corynebacterium* (Int. J. Syst. Bacteriol., 41, 255(1991)), also includes bacteria belonging to the genus *Brevibacterium* that are closely related to bacteria belonging to the genus *Corynebacterium*, and following are specifically exemplified (International Publication WO2010/005099):

*Corynebacterium acetoacidphilum*,
*Corynebacterium acetoglutamicum*,
*Corynebacterium alkanolyticum*,
*Corynebacterium callunae*,
*Corynebacterium glutamicum*,
*Corynebacterium lilium* (*Corynebacterium glutamicum*),
*Corynebacterium melassecola*,
*Corynebacterium thermoaminogenes*,
*Corynebacterium herculis*,
*Brevibacterium divaricatum* (*Corynebacterium glutamicum*),
*Brevibacterium flavum* (*Corynebacterium glutamicum*),
*Brevibacterium immariophilum*,
*Brevibacterium lactofermentum* (*Corynebacterium glutamicum*),
*Brevibacterium roseum*,
*Brevibacterium saccharolyticum*,
*Brevibacterium thiogenitalis*,
*Brevibacterium album*,

*Brevibacterium cerinum*, and
*Microbacterium ammoniaphilum*.

NhoA may include a protein having an amino acid sequence having 70% or more, 80% or more, 90% or more, 95% or more, or 98% or 99% or more identity to the amino acid sequence of SEQ ID NO:2 and having the NhoA activity. Also the nhoA gene may include a DNA having a nucleotide sequence having 70% or more, 80% or more, 90% or more, 95% or more, or 98% or 99% or more identity to the nucleotide sequence of SEQ ID NO:3 and encoding the protein having the NhoA activity.

Homology (e.g., identity or similarity) between the amino acid sequences or between the nucleotide sequences can be determined, for example, by using the algorithm BLAST by Karlin and Altschul (Pro. Natl. Acad. Sci. USA, 90, 5873 (1993)) and FASTA by Pearson (Methods Enzymol., 183, 63 (1990)). Programs termed BLASTP and BLASTN were developed based on this algorithm BLAST (see ncbi.nlm-.nih.gov). Thus, the homology between the amino acid sequences and between the nucleotide sequences may be calculated using these programs using the default settings. Also, for example, a numerical value obtained by calculating as a percentage using a full length portion of a polypeptide encoded in ORF using software GENETYX Ver. 7.0.9 with a setting of Unit Size to Compare=2, which is available from Genetyx Corporation employing Lipman-Pearson method may be used as the homology between the amino acid sequences. The lowest value in the values derived from these calculations may be employed as the homology between the amino acid sequences and between the nucleotide sequences.

The nucleotide sequence of the nhoA gene can vary depending on the strain of the microorganism. Examples of the protein encoded by the nhoA gene may include proteins having an amino acid sequence having one or several amino acid substitutions, deletions, insertions or additions at one or multiple positions in the amino acid sequence of SEQ ID NO:2 and having the NhoA activity. Here, "several" varies depending on locations of the amino acid residues in a three-dimensional structure of a protein or types of the amino acid residues, but can be 1 to 100, 1 to 50, 1 to 30, most preferably 1 to 20, or 1 to 10 (for example, 1, 2, 3, 4, or 5). Such a substitution, deletion, insertion, addition or the like includes those due to a naturally occurring mutation (mutant or variant) based on individual difference of a microorganism having the nhoA gene.

The above substitution may be a conservative substitution that is a neutral mutation that causes no functional change. The conservative mutation is a mutation in which the substitution occurs mutually between Phe, Trp and Tyr when a site to be substituted is an aromatic amino acid, between Leu, Ile and Val when a site to be substituted is a hydrophobic amino acid, between Gln and Asn when a site to be substituted is a polar amino acid, between Lys, Arg and His when a site to be substituted is a basic amino acid, between Asp and Glu when a site to be substituted is an acidic amino acid, and between Ser and Thr when a site to be substituted is an amino acid having a hydroxyl group. More specifically, the conservative substitution may include the substitution from Ala to Ser or Thr, the substitution from Arg to Gln, His or Lys, the substitution from Asn to Glu, Gln, Lys, His or Asp, the substitution from Asp to Asn, Glu or Gln, the substitution from Cys to Ser or Ala, the substitution from Gln to Asn, Glu, Lys, His, Asp or Arg, the substitution from Glu to Gly, Asn, Gln, Lys or Asp, the substitution from Gly to Pro, the substitution from His to Asn, Lys, Gln, Arg or Tyr, the substitution from Ile to Leu, Met, Val or Phe, the substitution from Leu to Ile, Met, Val or Phe, the substitution from Lys to Asn, Glu, Gln, His or Arg, the substitution from Met to Ile, Leu, Val or Phe, the substitution from Phe to Trp, Tyr, Met, Ile or Leu, the substitution from Ser to Thr or Ala, the substitution from Thr to Ser or Ala, the substitution from Trp to Phe or Tyr, the substitution from Tyr to His, Phe or Trp, and the substitution from Val to Met, Ile or Leu.

The nhoA gene may also be a DNA that hybridizes with the nucleotide sequence complementary to the nucleotide sequence of SEQ ID NO:3 under a stringent condition and encodes the protein having the NhoA activity. Here, "stringent condition" can mean when a so-called specific hybrid is formed while a non-specific hybrid is not formed. One example is a condition where polynucleotides having high homology (e.g., identity or similarity), for example, 70% or more, 80% or more, 90% or more, 95% or more, or 98% or more homology hybridize each other while polynucleotides having lower homology than that do not hybridize each other. Specifically, such a condition may include hybridization in 6×SSC (sodium chloride/sodium citrate) at about 45° C. followed by one or two or more washings in 0.2×SSC and 0.1% SDS at 50 to 65° C.

<2> Modification to Increase Activity to Form 3-Amino-4-Hydroxybenzoic Acid from Dihydroxyacetone Phosphate and Aspartate Semialdehyde A microorganism can be modified so as to increase the activity to form 3-amino-4-hydroxybenzoic acid (3,4-AHBA) from dihydroxyacetone phosphate (DHAP) and aspartate semialdehyde (ASA). Such modification can be accomplished by, for example, transforming a desired microorganism with a recombinant vector including a DNA encoding a protein having the activity to form 3,4-AHBA from DHAP and ASA. The protein having the activity to form 3,4-AHBA from DHAP and ASA is not particularly limited as long as the protein contributes to the formation of 3,4-AHBA from DHAP and ASA, and includes, for example, proteins having an enzyme activity to catalyze formation of a carbon-carbon bond between DHAP and ASA (hereinafter sometimes abbreviated as an "aldolase activity") and proteins having an enzyme activity to catalyze cyclization of a C7 compound obtained by forming the carbon-carbon bond between DHAP and ASA (hereinafter sometimes abbreviated as a 3-amino-4-hydroxybenzoic acid synthase activity). Hereinafter, both the above activities are sometimes referred to as the ability to biosynthesize 3,4-AHBA.

A gene encoding the protein having the enzyme activity to catalyze the formation of the carbon-carbon bond between DHAP and ASA may include a griI gene or a griI gene homolog (both the griI gene and the griI gene homolog are sometimes simply referred to as the griI gene) derived from *Streptomyces griseus*. The griI gene homolog can refer to a gene that is derived from another microorganism, exhibits high homology to the above gene derived from *Streptomyces griseus*, and encodes a protein having the aldolase activity. Such a gene can be found by a BLAST search. Examples thereof may include an nspI gene derived from *Streptomyces murayamaensis* (SEQ ID NO:18 and 19), fructose-bisphosphate aldolase (Accession no. YP_483282) and Fructose-bisphosphate aldolase (Accession no. YP_481172) derived from *Frankia sp.*, Fructose-bisphosphate aldolase (sanger-.ac.uk/cgi-bin/blast/submitblast/s —scabies) derived from *Streptomyces scabies*, fructose-bisphosphate aldolase (Accession no. Q39NQ9) derived from *Burkholderia* sp. 383, fructose-bisphosphate aldolase (Accession no. NP_247374) derived from *Methanococcus jannaschii*, and a dhnA gene (Accession no. NC_000913) derived from *Escherichia coli* (Journal of Biochemistry vol. 281, NO. 48, pp.36944-36951, supplementary data).

The gene encoding the protein having the enzyme activity to catalyze the cyclization of the C7 compound obtained by forming the carbon-carbon bond between DHAP and ASA may include a griH gene or a griH gene homolog (both the griH gene and the griH gene homolog are sometimes simply referred to as the griH gene) derived from *Streptomyces griseus*. The griH gene homolog can refer to a gene that is derived from another microorganism, exhibits high homology to the above gene derived from *Streptomyces griseus*, and encodes a protein having the 3-amino-4-hydrosybenzoic acid synthase activity. Such a gene can be found by BLAST search. Examples thereof may include an nspH gene derived from *Streptomyces murayamaensis* (SEQ ID NO:20 and 21), 3-dehydroquinate synthase (Accession no. YP_483283) and 3-dehydroquinate synthase (Accession no. YP_481171) derived from *Frankia* sp., 3-dehydroquinate synthase (Accession no.YP—366552) and 3-dehydroquinate synthase (Accession no. YP_366553) derived from *Burkholderia* sp. 383, 3-dehydroquinate synthase (sanger.ac.uk/cgi-bin/blast/submitblast/s_scabies) derived from

*Streptomyces scabies*, and 3-dehydroquinate synthase (Accession no. NP_248244) derived from *Methanococcus jannaschii* (Journal of Biochemistry vol. 281, NO. 48, pp.36944-36951, supplementary data).

GriI and GriH or the griI gene and the griH gene derived from any organism can be used. For example, they can be derived from microorganisms such as the bacteria or actinomycetes described above. Examples of actinomycetes can include microorganisms belonging to the genus *Streptomyces*. Examples of the microorganisms belonging to the genus *Streptomyces* can include *Streptomyces griseus*, *Streptomyces murayamaensis*, *Streptomyces lividans*, and *Streptomyces* scabies. GriI and GriH or the griI gene and the griH gene can be derived from the same microorganism or different microorganisms.

A GriI homolog can have an amino acid sequence having 70% or more, 80% or more, 90% or more, 95% or more, 98% or 99% or more identity to SEQ ID NO:9 or 18 that is an amino acid sequence of a protein encoded by the above griI gene and having the aldolase activity. Examples thereof may include SEQ ID NOS:9, 11, 13, 15, 17, 19, and 21 in the international Publication WO2010/005099. The griI gene homolog can include a nucleotide sequence having 70% or more, 80% or more, 90% or more, 95% or more, 98% or 99% or more identity to SEQ ID NO:10 or 19, and can encode a protein having aldolase activity. Examples thereof may include SEQ ID NOS:8, 10, 12, 14, 16, 18 and 20 in the international Publication WO2010/005099.

A GriH homolog can have an amino acid sequence having 70% or more, 80% or more, 90% or more, 95% or more, 98% or 99% or more identity to SEQ ID NO:11 or 20, is encoded by the above griH gene, and has 3-amino-4-hydroxybenzoic acid synthase activity. Examples thereof may include SEQ ID NOS:23, 25, 27, 29, 31, 33, and 35 in the international Publication WO2010/005099. Also, the griH gene homolog can have a nucleotide sequence having 70% or more, 80% or more, 90% or more, 95% or more, 98% or 99% or more identity to SEQ ID NO:12 or 21, and can encode a protein having 3-amino-4-hydroxybenzoiic acid synthase activity. Examples thereof may include SEQ ID NOS:22, 24, 26, 28, 30, 32, and 34 in the international Publication WO2010/005099.

A position or positions of an amino acid residue, when mutated, which do not influence activity in an amino acid sequence is evident to those of ordinary skill in the art, and a protein mutant may be made further with reference to a sequence alignment. Specifically, those skilled in the art can (1) compare amino acid sequences of a plurality of homolog proteins, (2) determine relatively conserved region(s) and relatively non-conserved region(s), then (3) predict region(s) capable of playing an important role for its function and region(s) incapable of playing an important role for its function from the relatively conserved region(s) and the relatively non-conserved region(s), respectively, and thus recognize correlativity of its structure/function. The international Publication WO2010/005099 discloses the alignment of the amino acid sequences of the above griI gene homologs (FIGS. 1 and 2 in International Publication WO2010/005099), the alignment of the amino acid sequences of the above griH gene homologs (FIGS. 3 and 4 in International Publication WO2010/005099), and their consensus (common) sequences (SEQ ID NOS:36 and 37 in International Publication WO2010/005099). The homologs of the griI gene include a gene encoding the amino acid sequence of SEQ ID NO:36 in International Publication WO2010/005099, and the homologs of the griH gene include a gene encoding the amino acid sequence of SEQ ID NO:37 in International Publication WO2010/005099).

The homology (e.g., identity or similarity) between the amino acid sequences and between the nucleotide sequences can be determined as described above.

The nucleotide sequence of the griI gene or the griH gene may vary depending on species and microbial strain of the microorganism. Thus, it is only necessary that the griI gene and the griH gene be able to enhance the ability to produce 3,4-AHBA in *Escherichia coli* by expressing them in *Escherichia coli*, e.g., augmenting their expression. For example, a protein encoded by the griI gene can have an amino acid sequence having one or several amino acid substitutions, deletions, insertions, additions or the like at one or multiple positions in the amino acid sequence of the protein encoded by the griI gene (SEQ ID NO:9 or 18) and have aldolase activity. Examples thereof may include SEQ ID NOS:9, 11, 13, 15, 17, 19, and 21 in the international Publication WO2010/005099. A protein encoded by the griI gene can have an amino acid sequence having one or several amino acid substitutions, deletions, insertions additions or the like at one or multiple positions in the amino acid sequence of the protein encoded by the griH gene (for example, SEQ ID NO:11 or 20) and have 3-amino-4-hydroxybenzoic acid synthase activity. Examples thereof may include SEQ ID NOS:23, 25, 27, 29. 31, 33, and 35 in the international Publication WO2010/005099. Here, "several" varies depending on locations of the amino acid residues in a three-dimensional structure of a protein or types of the amino acid residues, but can be 1 to 50, 1 to 20, 1 to 10 and 1 to 5. Such an amino acid substitution, deletion, insertion, addition or the like can include those that naturally occur (mutant or variant) based on individual difference or species difference of the microorganism having the griI gene or the griH gene, or the like. The substitution can be a conservative substitution that is neutral substitution in which a function is not changed. The conservative substitution is as described above.

Furthermore, degeneracy of the griI gene and the griH gene varies depending on a host to which such a gene is introduced. Thus, codons may be replaced with codons available in a desired microorganism. Likewise, the griI gene and the griH gene may be genes encoding proteins that are extended or truncated on an N terminal side and/or a C terminal side as long as the gene has a function to enhance the ability to produce 3,4-AHBA in a microorganism. For example, a length of extended or truncated residues is 50 or less, 20 or less, 10 or less, or 5 or less of amino acid residues. More specifically, the gene may be a gene encoding a protein in which 50 to 5 amino acid residues on the N terminal side or 50 to 5 amino acid residues on the C terminal side have been extended or truncated.

Such a gene that is homologous to the griI gene or the griH gene can be acquired by, for example, modifying the gene encoding an amino acid sequence by site-specific mutagenesis so that an amino acid residue at a particular position of the encoded protein can include the substitution, deletion, insertion or addition. Such a homologous gene can also be acquired by conventionally known mutation treatments, such as by treating the griI gene or the griH gene with hydroxylamine and the like in vitro or treating a microorganism carrying the gene with ultraviolet ray or a mutating agent such as N-methyl-N'-nitro-N-nitrosoguanidine (NTG) or ethyl methanesulfonate (EMS) generally used for the mutation treatment, error prone PCR (Cadwell, R. C. PCR Meth. Appl. 2, 28(1992)), DNA shuffling (Stemmer, W. P. Nature 370, 389 (1994)), and StEP-PCR (Zhao, H. Nature Biotechnol. 16, 258 (1998)). Utilizing these treatments, a mutation can be artificially introduced into the griI gene or the griH gene by gene recombination to acquire a gene encoding an enzyme with high activity.

The griI gene can also be a DNA that hybridizes under a stringent condition with a nucleotide sequence complementary to a nucleotide sequence of the griI gene or its homolog gene (e.g., SEQ ID NO:10 or 19, or SEQ IDS NO:8, 10, 12, 14, 16, 18 or 20 in the international Publication WO2010/005099) and encodes a protein having the aldolase activity. The griH gene can also be a DNA that hybridizes under a stringent condition with a nucleotide sequence complementary to a nucleotide sequence of the griH gene or its homolog gene (e.g., SEQ ID NO:12 or 21, or SEQ ID NOS:22, 24, 26, 28, 30, 32 or 34 in the international Publication WO2010/005099) and encodes a protein having the 3-amino-4-hydroxybenzoic acid synthase activity. The "stringent condition" is the same as described above.

The descriptions concerning the above gene homologs and the conservative substitution can be applied to the other genes described herein in the same manner.

Whether these griI gene and griH gene and the homolog genes thereof encode or do not encode the protein that enhances the ability to produce 3,4-AHBA can be confirmed by introducing these genes into a bacterium and the like having a gene encoding mutated aspartokinase in which feedback inhibition is canceled, and examining whether the activity of forming 3,4-AHBA is enhanced or not. In such a case, the effect can be verified more clearly by quantifying 3,4-AHBA using reverse phase chromatography according to, for example, Suzuki, et al.'s method [J. Bio. Chem., 281, 823-833 (2006)].

<3> Recombinant Vector

A recombinant vector that can be used can be obtained by introducing a desired gene into an expression vector. For example, when using nhoA, griI, and griH are used together, they may be each carried on a separate recombinant vector for transformation, or they may be linked via an appropriate spacer and carried on the same recombinant vector, as long as they can be expressed. The griI gene and the griH gene may be derived from the same microorganism or different microorganisms. When the griI gene and the griH gene are derived from the same microorganism and located in close proximity on a chromosome, a DNA fragment including both griI and griH may be cut out and carried on a vector.

The recombinant vector generally has a promoter, the aforementioned DNA, e.g., nhoA, griI and griH, and regulatory regions (operator and terminator) necessary for expression of the genes in the recombinant microorganism at appropriate positions so that they can function.

An expression vector that can be used as a recombinant vector is not particularly limited, as long as it can function in the chosen microorganism, and can be a plasmid that autonomously replicates out of a chromosome or can be integrated into the chromosome in a bacterium. Specifically, examples of the expression vector may include pBR322, pHSG299, pHSG298, pHSG399, pHSG398, pSTV28, pSTV29 (pHSG and pSTV are available from Takara Bio Inc.), pMW119, pMW118, pMW219, MW218 (pMW series are available from Nippon Gene Co., Ltd.), and the like, which are plasmids capable of autonomously replicating in bacteria belonging to enteric bacteria groups when introduced into a bacterium belonging to the genus *Escherichia* or *Pantoea*. A phage DNA may be used as the vector in place of the plasmid. When introduced into a bacterium belonging to the genus *Corynebacterium*, examples of the expression vector may include pCRY30 (described in JP 3-210184-A), pCRY21, pCRY2KE, pCRY2KX, pCRY31, pCRY3KE and pCRY3KX (described in JP 2-72876-A and U.S. Pat. No. 5,185,262), pCRY2 and pCRY3 (described in JP 1-191686-A), pAM330 (described in JP 58-67679-A), pHM1519 (described in JP 58-77895-A), pAJ655, pAJ611 and pAJ1844 (described in JP 58-192900-A), pCG1 (described in JP 57-134500-A), pCG2 (described in JP 58-35197-A), pCG4 and pCG11 (described in JP 57-183799-A), pVC7 (described in JP 9-070291-A), pVK7 (described in JP 10-215883-A), which are plasmids capable of autonomously replicating in bacteria belonging to the genus *Corynebacterium*, and derivatives thereof.

The promoter is not particularly limited, and a promoter generally used for production of a foreign protein in a desired microorganism can be used. For example, a T7 promoter, a lac promoter, a trp promoter, a trc promoter, a tac promoter, a PR promoter and PL promoter of a lambda phage, a T5 promoter and the like are known in the use for the genus *Escherichia* or *Pantoea*. Strong promoters such as promoters for genes encoding PS 1 and PS2 that are cell surface proteins derived from the genus *Corynebacterium* (described in JP 6-502548-A) and a promoter for a gene encoding SlpA that is a cell surface protein derived from the genus *Corynebacterium* (described in JP 10-108675-A) may be included in the use for the genus *Corynebacterium*.

<4. Transformant>

The microorganism is not particularly limited as long as it is able to produce 3-amino-4-hydroxybenzoic acid and is modified so as to increase the activity of N-hydroxyarylamine O-acetyltransferase (NhoA), and can be a transformant. The transformant can be obtained by transforming with a recombinant vector that includes a DNA that encodes a protein having an activity to form 3-amino-4-hydroxybenzoic acid from dihydroxyacetone phosphate and aspartate semialdehyde.

A host microorganism can be a microorganism that can efficiently supply dihydroxyacetone phosphate, aspartate semialdehyde, and an acetyl group donor (e.g., acetyl CoA) that are substrates for biosynthesis of 3-acetylamino-4-hydroxybenzoic acid-type compounds. Aspartokinase (AK) in microorganisms is originally subjected to concerted feedback inhibition by an amino acid such as lysine. For example, *Escherichia coli* has aspartokinase III (AKIII) that is a non-conjugated enzyme and functions alone. AKIII in *Escherichia coli* is originally subjected to feedback inhibition by lysine. On the other hand, it is known that AK in a coryneform bacterium is a heteroprotein composed of an α-subunit and a β-subunit and coding regions of the α-subunit gene and the β-subunit gene are partially overlapped. AK in a coryneform bacterium is originally subjected to concerted feedback inhibition by lysine and threonine. A microorganism having an AK gene with a mutation that substantially cancels the feedback inhibition can be used.

The mutations capable of canceling the feedback inhibition by an amino acid such as lysine have been reported for aspartokinase derived from various microorganisms such as Escherichia coli, Corynebacterium glutamicum, Serratia marcescens and the like. For example, the mutation of glutamic acid at position 250 to lysine (E250K), the mutation of methionine at position 318 to isoleucine (M318I), the mutation of threonine at position 344 to methionine (T344M), the mutation of serine at position 345 to leucine (S345L), the mutation of threonine at position 352 to isoleucine (T352I) have been reported as the mutation capable of canceling the feedback inhibition by lysine in AKIII from Escherichia coli (see, e.g., Kikuchi et al., FEMS Microbiology Letters 173, 211-215 (1999), and Falco et al., Bio-Technology 13, 577-582 (1995)). The mutation capable of canceling the feedback inhibition in AK from a coryneform bacterium is explained by taking an α-subunit of wild-type AK derived from Corynebacterium glutamicum (Brevibacterium lactofermentum) ATCC 13869 (see, e.g., SEQ ID NO:38 in the international Publication WO2010/005099) as an example. Canceling the feedback inhibition in AK is accomplished by substituting the alanine residue at position 279 from the N terminus on the α-subunit with a threonine residue, or substituting the threonine residue at position 311 from the N terminus with an isoleucine residue, or substituting the serine residue at position 301 from the N terminus with a tyrosine residue, or substituting the threonine residue at position 380 from the N terminus with an isoleucine residue, or substituting the threonine residue at position 308 from the N terminus with an isoleucine residue, or substituting the arginine residue at position 320 from the N terminus with a glycine residue, or substituting the glycine residue at position 345 from the N terminus with an aspartic acid (the international Publication WO94/25605, the international Publication WO00/63388, U.S. Pat. No. 6,844,176, International Publication WO01/049854 and the like). The amino acid sequence of AK even derived from the wild type is different in several amino acid residues from the amino acid sequence of SEQ ID NO:38 in the international Publication WO2010/005099, depending on type and strain of the coryneform bacterium from which the AK is derived. AK may be such an allelic variant. The definition of such mutations is the same as that described for aforementioned griI and griH.

The microorganism having the AK gene in which the mutation as described above has been introduced can be used. The amino acid sequence of AK even derived from the wild type is different in several amino acid residues depending on the type and the strain of the coryneform bacterium from which the AK is derived. Such an allelic variant may be used. The position to be modified for canceling the feedback inhibition in the allelic variant can be identified by performing a sequence alignment. The modification for canceling the feedback inhibition in AK can be accomplished by a method publicly known to those skilled in the art, for example, acquisition of a mutant strain having resistance to a lysine analog such as 2-aminoethylcysteine or introduction of site-specific mutagenesis by gene replacement utilizing homologous recombination. Also, a microorganism with an augmented activity of a mutated AK in which the feedback inhibition was canceled can also be obtained by transforming the microorganism with a plasmid that includes a mutated AK gene in which the feedback inhibition was canceled.

The expression of a pyruvate carboxylase gene may further be augmented in the microorganism having the mutated AK gene in which the feedback inhibition was canceled.

According to methods known in the art, the microorganism can be transformed with a recombinant vector that includes a DNA encoding a protein able to form 3-amino-4-hydroxybenzoic acid from dihydroxyacetone phosphate and aspartate semialdehyde. For example, a protoplast method (Gene, 39, 281-286 (1985)), an electroporation method (Bio/Technology, 7, 1067-1070 (1989)), and the like can be used. When transformation for canceling the feedback inhibition in AK is performed, either the transformation for conferring the activity of forming 3,4-AHBA or the transformation for canceling the feedback inhibition in AK may be performed first.

<5> Methods for Producing 3-acetyamino-4-hydroxybenzoic Acid-Type Compound, and Methods for Producing 3-amino-4-hydroxybenzoic Acid-Type Compound and Polymer Comprising 3-amino-4-hydroxybenzoic Acid-Type Compound as Component <5-1> Methods for Producing 3-acetyamino-4-hydroxybenzoic Acid-Type Compound A method for producing a 3-acetylamino-4-hydroxybenzoic acid-type compound is described, and includes steps of culturing the microorganism as described herein to form the 3-acetylamino-4-hydroxybenzoic acid-type compound. The 3-acetylamino-4-hydroxybenzoic acid-type compound can be biosynthesized from dihydroxyacetone phosphate, aspartate semialdehyde and an acetyl group donor (e.g., acetyl CoA). Therefore, the microorganism can efficiently supply the dihydroxyacetone phosphate, the aspartate semialdehyde and the acetyl group donor (e.g., acetyl CoA), which are substrates in biosynthesis of the 3-acetylamino-4-hydroxybenzoic acid-type compound. Also, the microorganism may be cultured in a medium containing the dihydroxyacetone phosphate, the aspartate semialdehyde and the acetyl group donor in large amounts.

The 3-acetyamino-4-hydroxybenzoic acid-type compound includes 3-acetyamino-4-hydroxybenzoic acid (hereinafter sometimes abbreviated as "3,4-AcAHBA") having the following structure as well as a derivative and a salt thereof.

Chemical 3:

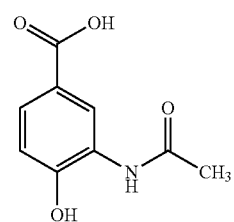

In the derivative of the 3-acetylamino-4-hydroxybenzoic acid-type compound, (1) either the carboxyl group at position 1, the acetylamino group at position 3, and/or the hydroxyl group at position 4, or a combination of these, is/are derivatized, (2) the carboxyl group at position 1, the acetylamino group at position 3, and the hydroxyl group at position 4 are kept and a hydrogen atom on at least one carbon atom at position 2, 5 or 6 is substituted with other atom or group, or (3), (1) and (2) are combined. Examples of the other atom or group in (2) above may include halogen atoms (e.g., a fluorine atom, a bromine atom, a chlorine atom, an iodine atom), alkyl groups (e.g., alkyl groups having 1 to 6 carbon atoms such as methyl, ethyl, propyl, butyl, pentyl, and hexyl), a hydroxyl group, an alkyloxy group (the alkyl moiety is the same as described above), an amino group, a mono- or di-alkylamino group (the alkyl moiety is the same as described above), a cyano group, a nitro group, a sulfonyl group, and a carboxyl group. Specifically, examples of the derivative in (1) above may include derivatives in which the carboxyl group at position 1 is derivatized (e.g., 3-amino-4-hydroxybenzaldehyde in which the carboxyl group in 3-acetylamino-4-hydroxybenzoic acid is aldehydated), derivatives in which the acetylamino group at position 3 is derivatized with the group such as the above alkyl group (e.g., 3-acetylalkylamino derivatives), and derivatives in which the hydroxyl group at position 4 is derivatized with the group such as the above alkyl group (e.g., 4-alkyloxy derivatives).

Base salts such as alkali metal (e.g., sodium, potassium, lithium) salts and alkali earth metal (e.g., calcium, magnesium) salts of carboxylic acid, and acid addition salts such as hydrochloride salts, sulfate salts, lead nitrate and phosphate salts are exemplified as salts.

The 3-acetylamino-4-hydroxybenzoic acid-type compound can be produced by culturing the microorganism and recovering the 3-acetylamino-4-hydroxybenzoic acid-type compound produced in the medium.

The medium for culturing the microorganism is not particularly limited as long as the desired microorganism is grown, and the microorganism can be cultured according to methods known in the art. For example, the microorganism can be cultured in an ordinary medium containing a carbon source, a nitrogen source, and inorganic ions. Organic trace nutrients such as vitamins and amino acids may be added if necessary in order to obtain higher proliferation. A cultivation temperature is generally 25 to 42° C., and it is desirable to control pH to 5 to 8. A cultivation time period is generally 20 to 90 hours.

It is desirable to perform the cultivation of the microorganism under a condition that controls oxygen supply. Specifically, it is desirable to keep oxygen at 2.0 ppm or less when microbial growth enters the logarithmic growth phase.

A recovery method used in steps of recovering and purifying the 3-acetylamino-4-hydroxybenzoic acid-type compound from the culture medium may be appropriately selected from known methods. For example, recovery can occur from a culture medium supernatant obtained by removing microbial cells by centrifugation or membrane filtration after adjusting pH of the culture medium to an acidic pH at which solubility of the 3-acetylamino-4-hydroxybenzoic acid-type compound is high. The recovery method of 3-acetylamino-4-hydroxybenzoic acid from the culture medium supernatant in which the microbial cells have been removed may include purification by a porous adsorbent, crystallization and precipitation.

The porous adsorbent can be a porous solid adsorbent having a large surface area, and specifically can include hydrophilic adsorbents typified by silica gel, alumina, zeolite, bauxite, magnesia, activated white earth, acrylic synthetic adsorbents, and the like, and hydrophobic adsorbents typified by vegetable charcoal, bone charcoal, activated charcoal and aromatic synthetic adsorbents, and the like. Any adsorbent can be used without particular limitation as long as the purity of the 3-acetylamino-4-hydroxybenzoic acid-type compound can be enhanced by adsorbing the impurities. In this regard, however, the impurities adsorbed by the porous adsorbent abundantly contain aromatic compounds mainly produced in the process of biochemical synthesis. Thus, the hydrophobic adsorbent typified by the activated charcoal and the aromatic synthetic adsorbent to which these compounds easily adsorb can be used. These hydrophobic adsorbents may be used alone or in combination of two or more.

When the activated charcoal is used, its raw material is not particularly limited, and may include, but is not particularly limited to, plant raw materials such as wood powder and palm shell, coal/petroleum-based raw materials such as smokeless coal, petroleum pitch and cokes, synthetic resin-based raw materials such as acrylic resins, phenol resins, epoxy resins and polyester resins. Shapes of the activated charcoal are powder, grain and fibrous, and secondary processed articles such as filters and cartridges, and that easily handled may be appropriately selected.

Meanwhile, when an aromatic synthetic adsorbent is used, the raw material thereof is not particularly limited, and for example, the porous resins such as 1) unsubstituted aromatic resins, 2) aromatic resins having a hydrophobic substituent(s), and 3) aromatic resins obtained by giving a special treatment to the unsubstituted aromatic resins can be used. Specific compounds may include, for example, styrene- and divinylbenzene-based resins.

As mentioned above, an objective of contacting the 3-acetylamino-4-hydroxybenzoic acid-type compound in the culture medium with the porous adsorbent is to adsorb the impurities to the porous adsorbent and to improve the purity of the 3-acetylamino-4-hydroxybenzoic acid-type compound. However, the 3-acetylamino-4-hydroxybenzoic acid-type compound which is an objective product is sometimes adsorbed together in no small part with the impurities to the porous adsorbent. Thus, it is also possible to isolate and recover the 3-acetylamino-4-hydroxybenzoic acid-type compound by contacting the 3-acetylamino-4-hydroxybenzoic acid-type compound in the culture medium to the porous adsorbent, then contacting the porous adsorbent with a polar organic solvent to detach the 3-acetylamino-4-hydroxybenzoic acid-type compound from the porous adsorbent and dissolve the 3-acetylamino-4-hydroxybenzoic acid-type compound in the polar organic solvent. The polar organic solvent can be an organic solvent composed of polar molecules having a high dielectric constant, and can be used without particular limitation as long as the 3-acetylamino-4-hydroxybenzoic acid-type compound can be detached from the porous adsorbent and the 3-acetylamino-4-hydroxybenzoic acid-type compound can be dissolved in the polar organic solvent. The polar organic solvent may be used alone or in combination with two or more at a desired combination ratio.

The crystallization or the precipitation can produce a crystal or a precipitate by evaporating the solvent in which an objective substance is dissolved to concentrate, or lowering the temperature, or keeping the concentration higher than a saturation solubility by adding a poor solvent to the solvent in which an objective substance is dissolved, and is not particularly limited including conventionally and publicly known methods. The produced crystal or precipitate can be separated by precipitation, filtration, centrifugation or the like.

<5-2> Methods for Producing 3-amino-4-hydroxybenzoic Acid-Type Compound

The present invention also provides a method for producing a 3-amino-4-hydroxybenzoic acid-type compound. This method includes the following:

(1) forming a 3-acetylamino-4-hydroxybenzoic acid-type compound by the aforementioned method; and (2) deacetylating the 3-acetylamino-4-hydroxybenzoic acid-type compound to form the 3-amino-4-hydroxybenzoic acid-type compound.

The 3-amino-4-hydroxybenzoic acid-type compound in the present invention includes 3-amino-4-hydroxybenzoic acid (hereinafter sometimes abbreviated as "3,4-AHBA") having the following structure as well as a derivative and a salt thereof.

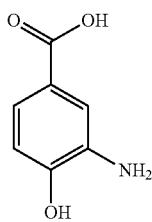

[Chemical 4]

In the derivative of the 3-amino-4-hydroxybenzoic acid-type compound, (1) the carboxyl group at position 1, the amino group at position 3, and/or the hydroxyl group at position 4 is derivatized, (2) the carboxyl group at position 1, the amino group at position 3 and the hydroxyl group at position 4 are kept and a hydrogen atom on at least one carbon atom at positions 2, 5 and 6 is substituted with other atom or group, or (3), (1) and (2) are combined. Examples of the other atom or group in (2) above may include halogen atoms (e.g., a fluorine atom, a bromine atom, a chlorine atom, an iodine atom), alkyl groups (e.g., alkyl groups having 1 to 6 carbon atoms such as methyl, ethyl, propyl, butyl, pentyl, hexyl and the like), a hydroxyl group, an alkyloxy group (the alkyl moiety is the same as described above), an amino group, a mono- or di-alkylamino group (the alkyl moiety is the same as described above), a cyano group, a nitro group, a sulfonyl group, and a carboxyl group. Specifically, examples of the derivative in (1) above may include derivatives in which the carboxyl group at position 1 is derivatized (e.g., 3-amino-4-hydroxybenzaldehyde in which the carboxyl group in 3-amino-4-hydroxybenzoic acid is aldehydated), derivatives in which the amino group at position 3 is derivatized with the group such as the above alkyl group (e.g., 3-alkylamino derivatives), and derivatives in which the hydroxyl group at position 4 is derivatized with the group such as the above alkyl group (e.g., 4-alkyloxy derivatives).

Base salts such as alkali metal (e.g., sodium, potassium, lithium) salts and alkali earth metal (e.g., calcium, magnesium) salts of carboxylic acid, and acid addition salts such as hydrochloride salts, sulfate salts, lead nitrate and phosphate salts are exemplified as salts.

The step (1) in the above method can be carried out in the same manner as in the aforementioned method for producing the 3-acetylamino-4-hydroxybenzoic acid-type compound.

The deacetylation in the step (2) in the above method can be carried out in any method known in the art. For example, the deacetylation can be carried out by hydrolysis utilizing an acid or a base. The acid is not particularly limited as long as a deacetylation reaction of Ac-AHBA-type compounds progresses, and can be a strong acid such as hydrochloric acid, sulfuric acid, nitric acid, phosphoric acid, and the like. The base is not particularly limited as long as the deacetylation reaction of Ac-AHBA-type compounds progresses, and it can be capable of increasing the reactivity of the deacetylation reaction to use a strong base such as sodium hydroxide, potassium hydroxide, calcium hydroxide, barium hydroxide, lithium hydroxide, and the like. The obtained 3-amino-4-hydroxybenzoic acid-type compound may be recovered and purified. The recovery and the purification of the 3-amino-4-hydroxybenzoic acid-type compound can be carried out in the same manner as in the recovery and the purification of the 3-acetylmino-4-hydroxybenzoic acid-type compound as described above.

<5-3> Methods for Producing Polymer Having 3-amino-4-hydroxybenzoic Acid-Type Compound as Component The present invention also provides a method for producing a polymer including a 3-amino-4-hydroxybenzoic acid-type compound as a component. This method includes the following:

(1') forming the 3-amino-4-hydroxybenzoic acid-type compound by the aforementioned method; and (2') polymerizing the 3-amino-4-hydroxybenzoic acid-type compound to obtain a polymer containing the 3-amino-4-hydroxybenzoic acid-type compound as a component.

The step (1') can be carried out in the same manner as in the aforementioned method for producing the 3-amino-4-hydroxybenzoic acid-type compound.

The step (2') can be carried out in any method known in the art. For example, the 3-amino-4-hydroxybenzoic acid-type compound obtained by the aforementioned method can be polymerized by condensation polymerization in a non-oxidizing solvent acid such as methanesulfonic acid or polyphosphoric acid at high temperature (see, e.g., WO91/01304). In the production method of a polymer according to the present invention, the 3-amino-4-hydroxybenzoic acid-type compound may be polymerized with other constituents of a polymer. Examples of the other constituents include terephthalic acid and bisphenol A, or terephthalic acid and p-phenylenediamine. Polymerizing method can be practiced by utilizing various known methods (U.S. Pat. Nos. 5,142,021, 5,219,981 and 5,422,416, and Kricheldorf et. al., (1992) Makromol. Chem., 193, 2467-2476, and Marcos-Fernandez et. al., (2001) Polymer, 42, 7933-7941). Examples of the polymer that includes a 3-amino-4-hydroxybenzoic acid-type compound as a component which is produced by the method as described herein include polybenzoxazole polymers, polyesters and polyamides.

EXAMPLES

The present invention will be described below with reference to the following non-limiting Examples. Chosen host microorganisms can efficiently supply dihydroxyacetone phosphate, aspartate semialdehyde, and acetyl CoA that is the acetyl group donor, which are substrates in biosynthesis of a 3-acetylamino-4-hydroxybenzoic acid-type compound.

Example 1

Construction of 3,4-AcAHBA-producing bacterium by introducing 3,4-AHBA synthetase gene group derived from *Streptomyces griseus* and nhoA gene derived from *Escherichia coli* into *Escherichia coli*, and evaluation of amount of accumulated 3,4-AcAHBA (1) Search of Enzyme that Catalyzes N-Acetylation of 3,4-AHBA Based on Genomic Information of *Escherichia coli*

It has been reported that arylamine N-acetyltransferase (convertible term: NatA; NCBI accession ID: BAF46971.1) catalyzes an N-acetylation reaction of 3,4-AHBA in *Streptomyces griseus* IFO13350 strain (Suzuki et. al., (2007) J. Bacteriol., 189, 2155-2159). An amino acid sequence of NatA is shown as SEQ ID NO:1. In order to search an enzyme having the same function as that in NatA, sequences exhibiting homology to NatA were searched from genomic information of *Escherichia coli* K-12 strain. As a result of searching utilizing published database (EcoCyc, ecocyc.org, Keseler et al., (2005) Nucleic Acids Res., 33, 334-337) and using BLASTP, N-hydroxyarylamine O-acetyltransferase from *Escherichia coli* K-12 strain (convertible term: NhoA, EC: 2.3.1.118, NCBI accession ID: NP_415980.1) was found to exhibit 49% homology to NatA derived from *Streptomyces griseus* IFO13350 strain. An amino acid sequence of NhoA and a nucleotide sequence of a gene encoding NhoA (convertible term: nhoA: GenBank accession No.: NC_000913.2, nucleotides 1532048 to 1532893, GI: 947251) are shown as SEQ ID NO:2 and SEQ ID NO:3, respectively.

(2) Construction of Plasmid for Expressing nhoA Gene

An expression plasmid for expressing the nhoA gene in *Escherichia coli* was constructed by the following procedure. PCR with genomic DNA from *Escherichia coli* BW25113 strain as a template was carried out using the synthesized oligonucleotide having a restriction enzyme recognition sequence for HindIII at the 3' terminus and shown as SEQ ID NO:4 and further the synthesized oligonucleotide having a restriction enzyme recognition sequence for EcoRI at the 3' terminus and shown as SEQ ID NO:5 as primers and using PrimeStar GXL polymerase (supplied from Takara). A reaction solution was prepared according to a composition attached to the kit, and 30 cycles of the reaction at 98° C. for 10 seconds, 55° C. for 15 seconds and 68° C. for 60 seconds were carried out. As a result, a PCR product of about 1.1 kbp including a native promoter of the nhoA gene and a nhoA gene fragment was obtained. This fragment was digested with EcoRI and HindIII, and subsequently cloned into pUC19 (supplied from Takara) digested with the same restriction enzymes. The resulting vector was designated as pUC19-NhoA. The full length sequence of pUC19-NhoA is shown as SEQ ID NO:6.

(3) Construction of Expression Plasmid pSTV28-Ptac-Ttrp

An expression plasmid pSTV28-Ptac-Trp was constructed to impart an ability to produce 3,4-AHBA to *Escherichia coli*. First, a DNA fragment comprising a tac promoter (convertible term: Ptac) region (deBoer, et al., (1983) Proc. Natl. Acad. Sci. U.S.A., 80, 21-25) and a terminator region of a tryptophan operon (convertible term: Ttrp) derived from *Escherichia coli* (Wu et al., (1978) Proc. Natl. Acad. Sci. U.S.A., 75, 5442-5446) and having a KpnI site at the 5' terminus and a BamHI site at the 3' terminus was chemically synthesized (the nucleotide sequence is shown as SEQ ID NO:7). The resulting DNA fragment was digested with KpnI and BamHI to obtain a DNA fragment including Ptac and Ttrp. The purified DNA fragment was ligated to pSTV28 (supplied from Takara Bio Inc.) digested with KpnI and BamHI by a ligation reaction with DNA ligase. The resulting plasmid was designated as pSTV28-Ptac-Ttrp (the nucleotide sequence is shown as SEQ ID NO:8). An objective gene can be expressed and amplified by cloning the objective gene downstream of Ptac of this plasmid.

(4) Chemical Synthesis of griI Gene and griH Gene Corresponding to Codon Usage in *Escherichia coli*

It has been reported that the synthesis of 3,4-AHBA is catalyzed by a 3,4-AHBA synthetase gene group consisting of aldolase (convertible term: SGR_4249, GriI) and 3,4-AHBA synthase (convertible term: SGR_4248, GriH) in *Streptomyces griseus* IFO13350 strain (Suzuki et. al., (2006) J. Biol. Chem., 281, 36944-36951). GriI is encoded by the griI gene (GenBank accession no. AB259663.1, nucleotides 13956 to 14780; GI: 117676060). The amino acid sequence of the GriI protein and a nucleotide sequence of the griI gene are shown as SEQ ID NO:9 and SEQ ID NO:10, respectively. Also, GriH is encoded by the griH gene (GenBank accession no. AB259663.1, nucleotides 12690 to 13880; GI: 117676059). The amino acid sequence of the GriH protein and a nucleotide sequence of the griH gene are shown as SEQ ID NO:11 and SEQ ID NO:12, respectively.

In order to efficiently express the griI gene and griH gene in *Escherichia coli*, the sequences of the griI gene and the griH gene were changed so as to correspond to codon usage in *Escherichia coli*, designed so as to express as an operon, and this was designated as EcGriIH. Restriction enzyme recognition sequences for EcoRI and HindIII were added to the 5' terminus and the 3' terminus of EcGriIH, respectively, and this fragment was chemically synthesized (shown as SEQ ID NO:13). EcGriIH, both termini of which the restriction enzyme recognition sequence had been added to, was digested with EcoRI and HindIII, and subsequently cloned into pUC57 (supplied from Genscript) which had been digested with the same restriction enzymes. The resulting vector was designated as pUC57-EcGri. The full length sequence of pUC57-EcGri is shown as SEQ ID NO:14.

(5) Construction of Plasmid for Expressing griI Gene and griH Gene

An expression plasmid for expressing the griI gene and the griH gene in *Escherichia coli* was constructed using the following procedure. PCR with pUC57-EcGri as a template was carried out using the synthesized oligonucleotide represented by SEQ ID NO:15 and further the synthesized oligonucleotide represented by SEQ ID NO:16 as primers and using PrimeStar GXL polymerase (supplied from Takara). A reaction solution was prepared according to a composition attached to the kit, and 30 cycles of the reaction at 98° C. for 10 seconds, 55° C. for 15 seconds and 68° C. for 150 seconds were carried out. As a result, a PCR product of about 2.1 kbp including an EcGriIH gene fragment was obtained. Subsequently, the purified EcGriIH gene fragment was ligated to pSTV28-Ptac-Ttrp digested with SmaI using In-Fusion HD Cloning Kit (supplied from Clontech). The resulting plasmid for expressing the griIH gene was designated as pSTV28-EcGri. The full length sequence of pSTV28-EcGri is shown as SEQ ID NO:17.

(6) Construction of 3,4-AcAHBA-Producing Bacterium

Competent cells of *Escherichia coli* BW25113 strain were prepared, and then pSTV28-EcGri was introduced thereto by electroporation. Subsequently the cells were uniformly applied onto an LB plate containing 30 mg/L of chloramphenicol, and cultured at 37° C. for 18 hours. A transformant exhibiting resistance to chloramphenicol was obtained from the resulting plate. A strain in which pSTV28-EcGri had been introduced into *Escherichia coli* BW25113 strain was designated as BW25113/pSTV28-EcGri strain. Subsequently, competent cells of BW25113/pSTV28-EcGri strain were prepared, and then pUC19 or pUC19-NhoA was intro duced by the electroporation. The cells were uniformly applied onto an LB plate containing 30 mg/L of chloramphenicol and 100 mg/L of ampicillin, and cultured at 37° C. for 18 hours. A transformant exhibiting resistance to both chloramphenicol and ampicillin was obtained from the resulting plate. A strain in which pUC19 had been introduced into BW25113/pSTV28-EcGri strain was designated as BW25113/pSTV28-EcGri/pUC19 strain. A strain in which pUC19-NhoA had been introduced into BW25113/pSTV28-EcGri strain was designated as BW25113/pSTV28-EcGri/pUC19-NhoA strain.

(7) 3,4-AcAHBA-Producing Culture

Microbial cells from BW25113/pSTV28-EcGri/pUC19 strain and BW25113/pSTV28-EcGri/pUC19-NhoA strain were uniformly applied onto an LB plate containing 30 mg/L of chloramphenicol and 100 mg/L of ampicillin, and cultured at 37° C. for 18 hours. One loopful of microbial cells obtained from the resulting plate was inoculated to 4 mL of MS glucose/Asp medium containing 30 mg/L of chloramphenicol and 100 mg/L of ampicillin in a test tube, and cultured on a reciprocal shaking cultivation apparatus at 30° C. for 48 hours. A composition of the MS glucose/Asp medium is as described in the following Table 1.

TABLE 1

Table 1. Composition of MS glucose/Asp medium

| Component | Final concentration |
|---|---|
| Glucose | 40 (g/L) |
| $(NH_4)_2SO_4$ | 24 (g/L) |
| Aspartic acid | 5 (g/L) |
| $KH_2PO_4$ | 1 (g/L) |
| $MgSO_4 \cdot 7H_2O$ | 1 (g/L) |
| $FeSO_4 \cdot 7H_2O$ | 10 (mg/L) |
| $MnSO_4 \cdot 7H_2O$ | 82 (mg/L) |
| Bacto-yeast extract | 2 (g/L) |
| $CaCO_3$ | 50 (g/L) |

The medium was adjusted to pH 7.0 with KOH, and autoclaved at 121° C. for 20 minutes. But, glucose and $MgSO4.7H_2O$ were mixed and separately sterilized. $CaCO_3$ was added after dry-heat sterilization.

Figure 1B:
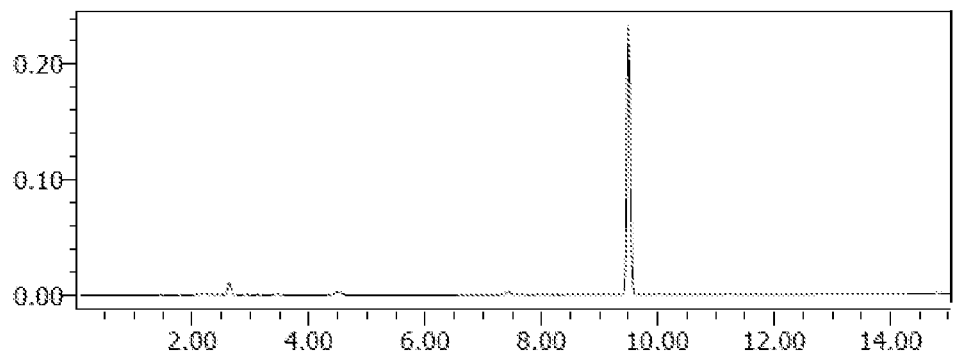
Figure 1C:
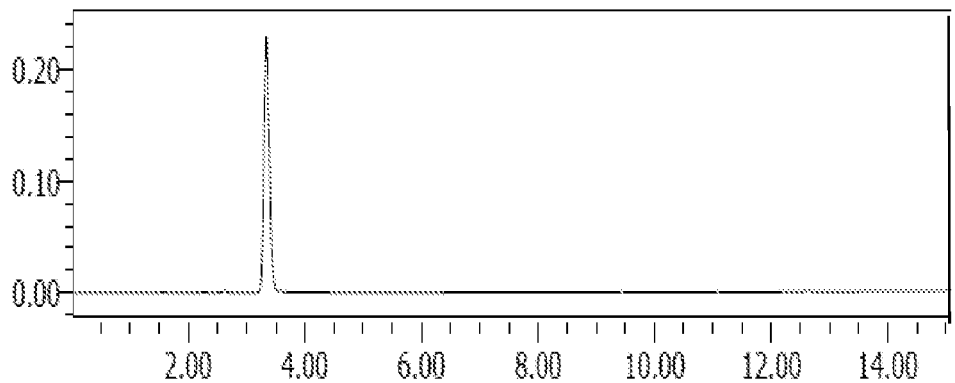

(8) Analysis of Molecular Weight of Compound (R.T., 9.5 Minutes) Converted from 3,4-AHBA Charts obtained from reverse phase column chromatography for culture supernatants of BW25113/pSTV28-EcGri/pUC19 strain and BW25113/pSTV28-EcGri/pUC19-NhoA strain described in Example 1 (7) and a 3,4-AHBA standard preparation (Cat No. A0859 supplied from Tokyo Chemical Industry Co., Ltd.) are shown in FIG. 1 (The analysis condition was described in Suzuki et. al., (2006) J. Biol. Chem., 281, 36944-36951). No 3,4-AHBA was detected in the culture supernatant of BW25113/pSTV28-EcGri/pUC19-NhoA strain, and the height of a peak detected at retention time (R.T.) of 9.5 minutes was found to increase compared with that of BW25113/pSTV28-EcGri/pUC19 that was a control. This suggested that 3,4-AHBA was converted into a compound detected at R.T. of 9.5 minutes by overexpressed NhoA.

The molecular weight of the compound (R.T., 9.5 minutes) converted from 3,4-AHBA which was contained in the culture supernatant after the cultivation of cells from BW25113/pSTV28-EcGri/pUC19-NhoA strain was analyzed by LC/MS. The analysis condition is as follows.

Column: Inertsil ODS-3 2 μm, 2.1×75 mm (supplied from GL Science)
Mobile phase: A=0.1% formic acid/$H_2O$
B=0.1% formic acid/acetonitrile
Gradient Program

| 0 minute | A/B = 100/0 |
|---|---|
| 3 minutes | A/B = 100/0 |
| 23 minutes | A/B = 20/80 |
| 25 minutes | A/B = 20/80 |

Flow rate: 0.2 mL/minute
Column temperature: Room temperature (25° C.)
Detection wavelength: 254 nm (PDA)
MS ionization mode: ESI
Analysis machines: Agilent Infinity 1290 (LC)
Agilent Quadrupole LC/MS 6130 (MS)

As a result of the analysis, the m/z value of the converted compound (R.T., 9.5 minutes) was 195.1, and matched with the calculated m/s value of acetylated 3,4-AHBA (195.1). Hereinafter, the converted compound (R.T., 9.5 minutes) is referred to as 3,4-AcAHBA.

(9) Absorbance of Culture Medium and Quantification of Accumulated 3,4-AHBA and 3,4-AcAHBA in Culture Supernatant Optical density (OD) values of culture media of cells from BW25113/pSTV28-EcGri/pUC19 strain and BW25113/pSTV28-EcGri/pUC19-NhoA strain described in Example 1 (7) at 600 nm were measured using a spectrophotometer (HITACHI U-2900). 3,4-AHBA and 3,4-AcAHBA accumulated in a culture supernatant were separated by reverse phase column chromatography and their accumulated amounts were quantified (Suzuki et. al., (2006) J. Biol. Chem., 281, 36944-36951). The OD values of the culture media at 600 nm, the amount of accumulated 3,4-AHBA, and the amount of accumulated 3,4-AcAHBA were shown in Table 2. No 3,4-AHBA was detected and the amount of accumulated 3,4-AcAHBA increased in the culture supernatant of BW25113/pSTV28-EcGri/pUC19-NhoA strain compared with the culture supernatant of BW25113/pSTV28-EcGri/pUC19 strain that was the control. The sum of the concentration of 3,4-AHBA and the concentration of 3,4-AcAHBA in the culture supernatant of BW25113/pSTV28-EcGri/pUC19-NhoA strain was 1.67 times larger than that of BW25113/pSTV28-EcGri/pUC19 strain.

TABLE 2

Table 2. Accumulated amounts of 3,4-AHBA and 3,4-AcAHBA and their summation in culture supernatant of *Escherichia coli* transformed with 3,4-AHBA synthetase gene group derived from *Streptomyces griseus* and nhoA gene derived from *Escherichia coli*

| Strain name | OD (600 nm) | Amount of accumulated 3,4-AHBA (g/L) | Amount of accumulated 3,4-AcAHBA (g/L) | Sum of accumulated 3,4-AHBA and accumulated 3,4-AcAHBA (g/L) |
|---|---|---|---|---|
| BW25113/pSTV28-EcGri/pUC19 | 30.3 ± 1.3 | 0.08 ± 0.01 | 0.43 ± 0.01 | 0.51 ± 0.01 |
| BW25113/pSTV28-EcGri/pUC19-NhoA | 24.5 ± 0.6 | N.D. | 0.85 ± 0.03 | 0.85 ± 0.03 |

N.D.: not detected
Each value is represented as a mean value obtained from cultivations in triplicate.

Example 2

Construction of 3,4-AHBA producing bacterium by introducing 3,4-AHBA synthetase gene group derived from *Streptomyces murayamaensis* and nhoA gene derived from *Escherichia coli* into *Escherichia coli*, and evaluation of amount of accumulated 3,4-AcAHBA (1) Chemical Synthesis of nspI Gene and nspH Gene Corresponding to Codon Usage in *Escherichia coli*

It has been already known that the synthesis of 3,4-AHBA is catalyzed by the 3,4-AHBA synthetase gene group consisting of aldolase (convertible term: NspI; NCBI accession ID:BAJ08171.1) and 3,4-AHBA synthase (convertible term: NspH; NCBI accession ID:BAJ08172.1) in *Streptomyces murayamaensis* (Noguchi et. al., (2010) Nat. Chem. Biol., 6,641-643). NspI is encoded by the nspI gene (GenBank accession No. AB530136, nucleotides 8730 to 9584; GI: 296784943). The amino acid sequence of the NspI protein and the nucleotide sequence of the nspI gene are shown as SEQ ID NO:18 and SEQ ID NO:19, respectively. Also, NspH is encoded by the nspH gene (GenBank accession No. AB530136, nucleotides 9599 to 10702; GI: 296784944). The amino acid sequence of the NspH protein and the nucleotide sequence of the nspH gene are shown as SEQ ID NO:20 and SEQ ID NO:21, respectively.

In order to efficiently express the nspI gene and nspH gene in *Escherichia coli*, the sequences of the nspI gene and the nspH gene were changed so as to correspond to codon usage in *Escherichia coli*, designed so as to express as an operon, and this was designated as EcNspIH. Restriction enzyme recognition sequences for EcoRI and HindIII were added to the 5' terminus and the 3' terminus of EcNspIH, respectively, and this fragment was chemically synthesized. EcNspIH, both termini of which the restriction enzyme recognition sequence had been added to, was digested with EcoRI and HindIII, and then cloned into pUC57 (supplied from Genscript) digested with the same restriction enzymes. The resulting vector was designated as pUC57-EcNsp.

(2) Construction of Plasmid for Expressing nspI Gene and nspH Gene

An expression plasmid for expressing the nspI gene and the nspH gene in *Escherichia coli* was constructed using the following procedure. PCR with pUC57-EcNsp as a template was carried out using the synthesized oligonucleotides as primers and using PrimeStar GXL polymerase (supplied from Takara). A reaction solution was prepared according to a composition attached to the kit, and 30 cycles of the reaction at 98° C. for 10 seconds, 55° C. for 15 seconds and 68° C. for 150 seconds were carried out. As a result, a PCR product of about 2.1 kbp comprising an EcNspIH gene fragment was obtained. Subsequently, the purified EcNspIH gene fragment was ligated to pSTV28-Ptac-Ttrp [described in Example 1 (3)] digested with SmaI using In-Fusion HD Cloning Kit (supplied from Clontech). The resulting plasmid for expressing the nspIH gene was designated as pSTV28-EcNsp.

(3) Construction of 3,4-AcAHBA-Producing Bacterium

Competent cells of *Escherichia coli* BW25113 strain were prepared, and then pSTV28-EcNsp was introduced thereto by electroporation. The cells were uniformly applied onto an LB plate containing 30 mg/L of chloramphenicol, and cultured at 37° C. for 18 hours. A transformant exhibiting resistance to chloramphenicol was obtained from the resulting plate. A strain in which pSTV28-EcNsp had been introduced into *Escherichia coli* BW25113 strain was designated as BW25113/pSTV28-EcNsp strain. Subsequently, competent cells of BW25113/pSTV28-EcNsp strain were prepared, and pUC19 or pUC19-NhoA [described in Example 1 (2)] was introduced by electroporation. The cells were uniformly applied onto an LB plate containing 30 mg/L of chloramphenicol and 100 mg/L of ampicillin, and cultured at 37° C. for 18 hours. A transformant exhibiting resistance to both chloramphenicol and ampicillin was obtained from the resulting plate. A strain in which pUC19 had been introduced into BW25113/pSTV28-EcNsp strain was designated as BW25113/pSTV28-EcNsp/pUC19 strain. A strain in which pUC19-NhoA had been introduced into BW25113/pSTV28-EcNsp strain was designated as BW25113/pSTV28-EcNsp/pUC19-NhoA strain.

(4) Evaluation of 3,4-AcAHBA-Producing Culture

Microbial cells from BW25113/pSTV28-EcNsp/pUC19 strain and BW25113/pSTV28-EcNsp/pUC19-NhoA strain were uniformly applied onto an LB plate containing 30 mg/L of chloramphenicol and 100 mg/L of ampicillin, and cultured at 37° C. for 18 hours. One loopful of microbial cells obtained from the resulting plate was inoculated to 4 mL of MS glucose/Asp medium containing 30 mg/L of chloramphenicol and 100 mg/L of ampicillin in a test tube, and cultured on the reciprocal shaking cultivation apparatus at 30° C. for 48 hours. The composition of the MS glucose/Asp medium is as described in Table 1.

After the cultivation, OD values of the culture media at 600 nm were measured using the spectrophotometer (HITACHI U-2900). Also, 3,4-AHBA and 3,4-AcAHBA accumulated in the culture supernatant were separated by reverse phase column chromatography and their amounts were measured in the same manner as in Example 1. The OD values of the culture media at 600 nm, the amount of accumulated 3,4-AHBA, and the amount of accumulated 3,4-AcAHBA were shown in Table 3. No 3,4-AHBA was detected and the amount of accumulated 3,4-AcAHBA increased in the culture supernatant of BW25113/pSTV28-EcNsp/pUC19-NhoA strain compared with the culture supernatant of BW25113/pSTV28-EcNsp/pUC19 strain that was the control. The sum of the concentration of 3,4-AHBA and the concentration of 3,4-AcAHBA in the culture supernatant of BW25113/pSTV28-EcNsp/pUC19-NhoA strain was 1.69 times larger than that of BW25113/pSTV28-EcNsp/pUC19 strain.

TABLE 3

Table 3. Accumulated amounts of 3,4-AHBA and 3,4-AcAHBA and their summation in culture supernatant of *Escherichia coli* transformed with 3,4-AHBA synthetase gene group derived from *Streptomyces murayamaensis* and nhoA gene derived from *Escherichia coli*

| Strain name | OD (600 nm) | Amount of accumulated 3,4-AHBA (g/L) | Amount of accumulated 3,4-AcAHBA (g/L) | Sum of Accumulated 3,4-AHBA and accumulated 3,4-AcAHBA (g/L) |
|---|---|---|---|---|
| BW25113/pSTV28-EcNsp/pUC19 | 32.4 ± 2.2 | 0.24 ± 0.02 | 0.43 ± 0.03 | 0.67 ± 0.03 |
| BW25113/pSTV28-EcNsp/pUC19-NhoA | 25.1 ± 1.4 | N.D. | 1.13 ± 0.08 | 1.13 ± 0.08 |

N.D.: not detected
Each value is represented as a mean value obtained from cultivations in triplicate.

Example 3

Construction of 3,4-AcAHBA producing bacterium by introducing 3,4-AHBA synthetase gene group derived from *Streptomyces griseus* and nhoA gene derived from *Escherichia coli* into *Pantoea ananatis*, and evaluation of amount of accumulated 3,4-AcAHBA (1) Construction of Plasmid for Expressing nhoA Gene An expression plasmid for expressing the nhoA gene in *Pantoea ananatis* was constructed using the following procedure. PCR with genomic DNA from *Escherichia coli* BW25113 strain as a template was carried out using the synthesized oligonucleotide having a restriction enzyme recognition sequence for HindIII at the 3' terminus and represented by SEQ ID NO:4 and further the synthesized oligonucleotide having a restriction enzyme recognition sequence for EcoRI at the 3' terminus and represented by SEQ ID NO:5 as primers and using PrimeStar GXL polymerase (supplied from Takara). A reaction solution was prepared according to a composition attached to the kit, and 30 cycles of the reaction at 98° C. for 10 seconds, 55° C. for 15 seconds and 68° C. for 60 seconds were carried out. As a result, a PCR product of about 1.1 kbp comprising a native promoter of the nhoA gene and an nhoA gene fragment was obtained. This fragment was digested with EcoRI and HindIII, and then cloned into pMW219 (supplied from Takara) digested with the same restriction enzymes. The resulting vector was designated as pMW219-NhoA. The full length sequence of pMW219-NhoA is shown as SEQ ID NO:22.

(2) Construction of 3,4-AcAHBA-Producing Bacterium

Competent cells of *Pantoea ananatis* SC17 strain (described in JP 2006-230202-A) were prepared, and then pSTV28-EcGri was introduced thereto by electroporation. The cells were uniformly applied onto an LB plate containing 30 mg/L of chloramphenicol, and cultured at 30° C. for 24 hours. A transformant exhibiting resistance to chloramphenicol was obtained from the resulting plate. A strain in which pSTV28-EcGri had been introduced into *Pantoea ananatis* SC17 strain was designated as SC17/pSTV28-EcGri strain. Subsequently, competent cells of SC17/pSTV28-EcGri strain were prepared, and then pMW219 or pMW219-NhoA was introduced by electroporation. The cells were uniformly applied onto an LB plate containing 30 mg/L of chloramphenicol and 50 mg/L of kanamycin, and cultured at 30° C. for 24 hours. A transformant exhibiting resistance to both chloramphenicol and kanamycin was obtained from the resulting plate. A strain in which pMW219 had been introduced into SC17/pSTV28-EcGri strain was designated as SC17/pSTV28-EcNsp/pMW219 strain. A strain in which pMW219-NhoA had been introduced into SC17/pSTV28-EcGri strain was designated as SC17/pSTV28-EcGri/pMW219-NhoA strain.

(3) Evaluation of 3,4-AcAHBA-Producing Culture

Microbial cells from SC17/pSTV28-EcGri/pMW219 strain and SC17/pSTV28-EcGri/pMW219-NhoA strain were uniformly applied onto an LB plate containing 30 mg/L of chloramphenicol and 50 mg/L of kanamycin, and cultured at 30° C. for 24 hours. One loopful of microbial cells obtained from the resulting plate was inoculated to 4 mL of MS glucose/Asp medium containing 30 mg/L of chloramphenicol and 50 mg/L of kanamycin in a test tube, and cultured on the reciprocal shaking cultivation apparatus at 30° C. for 32 hours. The composition of the MS glucose/Asp medium is as described in Table 1.

After the cultivation, OD values at 600 nm of the culture media were measured using the spectrophotometer (HITACHI U-2900). Also, 3,4-AHBA and 3,4-AcAHBA accumulated in the culture supernatant were separated by reverse phase column chromatography and their amounts were measured in the same manner as in Example 1 (9). The OD values at 600 nm of the culture media, the amount of accumulated 3,4-AHBA, and the amount of accumulated 3,4-AcAHBA were shown in Table 4. No 3,4-AHBA was detected and the amount of accumulated 3,4-AcAHBA increased in the culture supernatant of SC17/pSTV28-EcGri/pMW219-NhoA strain compared with that in the culture supernatant of SC17/pSTV28-EcGri/pMW219 strain that was the control. The sum of the concentration of 3,4-AHBA and the concentration of 3,4-AcAHBA in the culture supernatant of SC17/pSTV28-EcGri/pMW219-NhoA strain was 2.46 times larger than that of SC17/pSTV28-EcGri/pMW219 strain.

TABLE 4

Table 4. Accumulated amounts of 3,4-AHBA and 3,4-AcAHBA and their summation in culture supernatant of *Pantoea ananatis* transformed with 3,4-AHBA synthetase gene group derived from *Streptomyces griseus* and nhoA gene derived from *Escherichia coli*

| Strain name | OD (600 nm) | Amount of accumulated 3,4-AHBA (g/L) | Amount of accumulated 3,4-AcAHBA (g/L) | Sum of accumulated 3,4-AHBA and accumulated 3,4-AcAHBA (g/L) |
|---|---|---|---|---|
| SC17/pSTV28-EcGri/pMW219 | 15.2 ± 0.6 | 0.39 ± 0.00 | N.D. | 0.39 ± 0.00 |
| SC17/pSTV28-EcGri/pMW219-NhoA | 16.8 ± 1.0 | N.D. | 0.96 ± 0.05 | 0.96 ± 0.05 |

N.D.: not detected
Each value is represented as a mean value obtained from cultivations in triplicate.

Example 4

Construction of 3,4-AcAHBA-producing bacterium by introducing 3,4-AHBA synthetase gene group derived from *Streptomyces griseus* and nhoA gene derived from *Escherichia coli* into *Corynebacterium glutamicum*, and evaluation of amount of accumulated 3,4-AcAHBA (1) Construction of Plasmid for Expressing nhoA Gene An expression plasmid for expressing the nhoA gene in *Corynebacterium glutamicum* was constructed using the following procedure. PCR with genomic DNA from *Escherichia coli* BW25113 strain as a template was carried out using the synthesized oligonucleotide having a restriction enzyme recognition sequence for HindIII at the 3' terminus and represented by SEQ ID NO:4 and further the synthesized oligonucleotide having a restriction enzyme recognition sequence for EcoRI at the 3' terminus and represented by SEQ ID NO:5 as primers and using PrimeStar GXL polymerase (supplied from Takara). A reaction solution was prepared according to a composition attached to the kit, and 30 cycles of the reaction at 98° C. for 10 seconds, 55° C. for 15 seconds and 68° C. for 60 seconds were carried out. As a result, a PCR product of about 1.1 kbp comprising a native promoter of the nhoA gene and an nhoA gene fragment was obtained. This fragment was digested with EcoRI and HindIII, and then cloned into pVC7 (described in JP 9-070291-A) digested with the same restriction enzymes. The resulting vector was designated as pVC7-NhoA. The full length sequence of pVC7-NhoA is shown as SEQ ID NO:23.

(2) Construction of 3,4-AcAHBA-Producing Bacterium

A plasmid pPK4griIH described in JP 2010-005099-A was used in order to express the griI gene and the griH gene in *Corynebacterium glutamicum*. pPK4griIH includes a sequence connecting the griI gene and the griH gene downstream of a promoter sequence of a cell surface protein gene derived from *Corynebacterium glutamicum* ATCC 13869 strain (Peyret et al., (1993) Mol. Microbiol., 9, 97-109), and is a plasmid capable of efficiently expressing the griI gene and the griH gene in *Corynebacterium glutamicum*. Competent cells of *Corynebacterium glutamicum* ATCC 13869 strain were prepared, and then pPK4griIH was introduced thereto by electroporation. The cells were then applied uniformly onto a CMDex plate containing 25 mg/L of kanamycin, and cultured at 30° C. for 24 hours. The composition of the CMDex plate is shown in following Table 5.

TABLE 5

Table 5. Composition of CMDex

| Component | Final concentration |
|---|---|
| Glucose | 5 (g/L) |
| $KH_2PO_4$ | 1 (g/L) |
| $MgSO_4 \cdot 7H_2O$ | 0.4 (g/L) |
| $FeSO_4 \cdot 7H_2O$ | 10 (mg/L) |
| $MnSO_4 \cdot 5H_2O$ | 10 (mg/L) |
| Polypeptone | 10 (g/L) |
| Bacto-yeast extract | 10 (g/L) |
| Urea | 3 (g/L) |
| Hydrolyzed soybean product (as total nitrogen content) | 1.2 (g/L) |
| Biotin | 10 (µg/L) |
| Agar | 20 (g/L) |

The pH value was adjusted to 7.5 with KOH. The components were autoclaved at 121° C. for 20 minutes, but agar was added after adjusting the pH value.

A transformant exhibiting resistance to kanamycin was obtained from the resulting plate. A strain in which pPK4griIH had been introduced into *Corynebacterium glutamicum* ATCC 13869 strain was designated as ATCC13869/pPK4griIH strain. Subsequently, competent cells of ATCC13869/pPK4griIH strain were prepared, and then pCV7 or pCV7-NhoA was introduced by electroporation. The cells were then applied uniformly onto a CMDex plate containing 20 mg/L of kanamycin and 5 mg/L of chloramphenicol, and cultured at 30° C. for 24 hours. A transformant exhibiting resistance to both kanamycin and chloramphenicol was obtained from the resulting plate. A strain in which pVC7 had been introduced into ATCC13869/pPK4griIH strain was designated as ATCC13869/pPK4griIH/pVC7 strain. A strain in which pVC7-NhoA had been introduced into ATCC13869/pPK4griIH strain was designated as ATCC13869/pPK4griIH/pVC7-NhoA strain.

(3) Evaluation of 3,4-AcAHBA-Producing Culture

Microbial cells from ATCC13869/pPK4griIH/pVC7 strain and ATCC13869/pPK4griIH/pVC7-NhoA strain were uniformly applied onto a CMDex plate containing 20 mg/L of kanamycin and 5 mg/L of chloramphenicol, and cultured at 30° C. for 24 hours. One loopful of microbial cells obtained from the resulting plate was inoculated to 4 mL of a medium for producing 3,4-AcAHBA and containing 20 mg/L of kanamycin and 5 mg/L of chloramphenicol in a test tube, and cultured on the reciprocal shaking cultivation apparatus at 30° C. for 56 hours. The composition of the medium for producing 3,4-AcAHBA is as described in following Table 6.

TABLE 6

Table 6. Composition of medium for producing 3,4-AcAHBA

| Component | Final concentration |
|---|---|
| Glucose | 100 (g/L) |
| $(NH_4)_2SO_4$ | 55 (g/L) |
| $KH_2PO_4$ | 1 (g/L) |
| $MgSO_4 \cdot 7H_2O$ | 1 (g/L) |
| $FeSO_4 \cdot 7H_2O$ | 10 (mg/L) |
| $MnSO_4 \cdot 7H_2O$ | 10 (mg/L) |
| Hydrolyzed soybean product (as total nitrogen content) | 1.05 (g/L) |
| Nicotine amide | 5 (mg/L) |
| Thiamine hydrochloride | 2 (mg/L) |
| Biotin | 0.5 (mg/L) |
| $CaCO_3$ | 50 (g/L) |

The pH value was adjusted to 7.5 with KOH. The components were autoclaved at 121° C. for 20 minutes, but glucose and $MgSO_4.7H_2O$ were mixed and sterilized separately. $CaCO_3$ was added after dry-heat sterilization.

After the cultivation, OD values at 600 nm of the culture media were measured using the spectrophotometer (HITACHI U-2900). Also, 3,4-AHBA and 3,4-AcAHBA accumulated in the culture supernatant were separated by reverse phase column chromatography and their amounts were measured in the same manner as in Example 1 (9). The OD values at 600 nm of the culture media, the amount of accumulated 3,4-AHBA, and the amount of accumulated 3,4-AcAHBA were shown in Table 7. No 3,4-AHBA was accumulated and the amount of accumulated 3,4-AcAHBA increased in the culture supernatant of ATCC13869/pPK4griIH/pVC7-NhoA strain compared with that in the culture supernatant of ATCC13869/pPK4griIH/pVC7 strain that was the control.

TABLE 7

Table 7. Accumulated amounts of 3,4-AHBA and 3,4-AcAHBA and their summation in culture supernatant of *Corynebacterium glutamicum* transformed with 3,4-AHBA synthetase gene group derived from *Streptomyces griseus* and nhoA gene derived from *Escherichia coli*

| Strain name | OD (600 nm) | Amount of accumulated 3,4-AHBA (g/L) | Amount of accumulated 3,4-AcAHBA (g/L) | Sum of Amount of accumulated 3,4-AHBA and accumulated 3,4-AcAHBA (g/L) |
|---|---|---|---|---|
| ATCC13869/pPK4griIH/pVC7 | 95.5 ± 2.4 | 0.48 ± 0.00 | N.D. | 0.48 ± 0.00 |
| ATCC13869/pPK4griIH/pVC7-NhoA | 97.5 ± 3.4 | N.D. | 0.48 ± 0.00 | 0.48 ± 0.00 |

N.D.: not detected
Each value is represented as a mean value obtained from cultivations in triplicate.

INDUSTRIAL APPLICABILITY

According to the present invention, it is possible to conveniently and efficiently produce acetylamino-hydroxybenzoic acid-type compounds that can easily be converted to amino-hydroxybenzoic acid-type compounds that are useful as intermediates for dyes, agricultural chemicals, pharmaceuticals and other organic synthesized products and as monomers of polybenzoxazoles. Therefore, for example, 3-acetylamono-4-hydroxybenzoic acid obtained as described herein is converted to 3-amino-4-hydroxybenzoic acid and then the converted 3-amino-4-hydroxybenzoic acid is polymerized to yield polybenzoxazole (PBO), thereby being capable of inexpensively providing PBO fibers and PBO films having high intensity, high elastic modulus and high heat resistance. The 3-acetylamino-4-hydroxybenzoic acid-type compound that is a stable compound and can easily be converted to the 3-amino-4-hydroxybenzoic acid-type compound that is a raw material can be produced by biosynthesis. Thus, the method as described herein is a process with low environmental load and is friendly for the global environment.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

We claim:

1. A method for producing 3-acetylamino-4-hydroxybenzoic acid or a salt thereof, comprising:
   a) culturing a microorganism so that 3-acetylamino-4-hydroxybenzoic acid or a salt thereof is produced, and
   b) collecting said 3-acetylamino-4-hydroxybenzoic acid or salt thereof;
   wherein the microorganism is transformed with a recombinant vector encoding a GriI protein, a GriH protein, or GriI and GriH proteins, and has increased formation of 3-amino-4-hydroxybenzoic acid from dihydroxyacetone phosphate and aspartate semialdehyde as compared to the same microorganism that does not comprise said recombinant vector, and
   wherein the microorganism is transformed with a recombinant vector encoding a N-hydroxyarylamine O-acetyltransferase (NhoA) protein and has increased NhoA activity as compared to the same microorganism that does not comprise said recombinant vector, and wherein said NhoA protein is selected from the group consisting of:
   (I) a protein comprising the amino acid sequence of SEQ ID NO: 2;
   (II) a protein comprising the amino acid sequence of SEQ ID NO: 2, but having no more than one to ten amino acid substitutions, deletions, insertions or additions, and wherein said protein has NhoA activity;
   (III) a protein comprising an amino acid sequence having 95% or more sequence identity to the amino acid sequence of SEQ ID NO:2 and having NhoA activity; and
   (IV) combinations thereof.

2. A method for producing 3-amino-4-hydroxybenzoic acid, or a salt thereof, comprising:

(1) producing the 3-acetylamino-4-hydroxybenzoic acid or the salt thereof by the method according to claim 1; and (2) deacetylating the 3-acetylamino-4-hydroxybenzoic acid or the salt thereof to form the 3-amino-4-hydroxybenzoic acid or the salt thereof.

3. A method for producing a polymer containing a 3-amino-4-hydroxybenzoic acid or a salt thereof as a component, comprising:

(1') forming the 3-amino-4-hydroxybenzoic acid or the salt thereof by the method according to claim 2; and (2') polymerizing the 3-amino-4-hydroxybenzoic acid or the salt thereof to obtain a polymer containing the 3-amino-4-hydroxybenzoic acid or the salt thereof as a component.

4. The method according to claim 3, wherein the polymer is a polybenzoxazole polymer.

5. The method according to claim 1, wherein the NhoA protein is encoded by a DNA selected from the group consisting of:

(i) a DNA comprising the nucleotide sequence of SEQ ID NO: 3;

(ii) a DNA that hybridizes under stringent conditions with the nucleotide sequence complementary to the nucleotide sequence of SEQ ID NO:3 and encodes a protein having NhoA activity;

(iii) a DNA comprising a nucleotide sequence having 95% or more sequence identity to the nucleotide sequence of SEQ ID NO:3 and encodes a protein having NhoA activity; and (iv) combinations thereof; and wherein the stringent conditions include hybridization in 6×SSC at 45° C. followed by one or more washings in 0.2×SSC and 0.1% SDS at 50 to 65° C.

6. The method according to claim 1, wherein the microorganism belongs to the genus *Escherichia*, the genus *Pantoea*, or the genus *Corynebacterium*.

7. The method according to claim 1, wherein the microorganism is *Escherichia coli, Pantoea ananatis*, or *Corynebacterium glutamicum*.

8. The method according to claim 1, wherein said recombinant vector encodes GriI and GriH proteins.

9. The method according to claim 1, wherein said GriI protein is selected from the group consisting of:

(A) a protein comprising the amino acid sequence of SEQ ID NO:9 or SEQ ID NO: 18;

(B) a protein comprising the amino acid sequence of SEQ ID NO: 9 or SEQ ID NO: 18, but having no more than one to ten amino acid substitutions, deletions, insertions or additions in said amino acid sequence and said protein having aldolase activity;

(C) a protein comprising an amino acid sequence having 95% or more sequence identity to the amino acid sequence of SEQ ID NO: 9 or SEQ ID NO: 18 and having aldolase activity; and (D) combinations thereof; and wherein said GriH protein is selected from the group consisting of:

(E) a protein comprising the amino acid sequence of SEQ ID NO: 11 or SEQ ID NO:20;

(F) a protein comprising the amino acid sequence of SEQ ID NO: 11 or SEQ ID NO:20, but having no more than one to ten amino acid substitutions, deletions, insertions or additions in said amino acid sequence and said protein having 3-amino-4- hydroxybenzoic acid synthase activity;

(G) a protein comprising an amino acid sequence having 95% or more sequence identity to the amino acid sequence of SEQ ID NO: 11 or SEQ ID NO:20 and having 3-amino-4-hydroxybenzoic acid synthase activity; and (H) combinations thereof.

10. The method according to claim 1, wherein said GriI protein is encoded by a DNA selected from the group consisting of:

(a) a DNA comprising the nucleotide sequence of SEQ ID NO: 10 or SEQ ID NO:19;

(b) a DNA that hybridizes under stringent conditions with the nucleotide sequence complementary to the nucleotide sequence of SEQ ID NO: 10 or SEQ ID NO: 19 and wherein said DNA encodes a protein having aldolase activity;

(c) a DNA that has 95% or more sequence identity to the nucleotide sequence of SEQ ID NO: 10 or SEQ ID NO: 19 and encodes a protein having aldolase activity; and wherein said GriH protein is encoded by a DNA selected from the group consisting of:

(d) a DNA comprising the nucleotide sequence of SEQ ID NO: 12 or SEQ ID NO:21;

(e) a DNA that hybridizes under stringent conditions with the nucleotide sequence complementary to the nucleotide sequence of SEQ ID NO:12 or SEQ ID NO: 21 and wherein said DNA encodes a protein having 3-amino-4-hydroxybenzoic acid synthase activity; and (f) a DNA that has 95% or more sequence identity to the nucleotide, sequence of SEQ ID NO:12 or SEQ ID NO:21 and encodes a protein having 3-amino-4-hydroxybenzoic acid synthase activity; and (g) combinations thereof; and wherein the stringent conditions include hybridization in 6×SSC at 45° C. followed by one or more washings in 0.2×SSC and 0.1% SDS at 50 to 65° C.

* * * * *